United States Patent [19]

Lynch et al.

[11] Patent Number: 4,990,076
[45] Date of Patent: Feb. 5, 1991

[54] PRESSURE CONTROL APPARATUS AND METHOD

[75] Inventors: Michael J. Lynch; G. Allen Turner; Mark Ehlert; Jim B. Surjaatmadja, all of Duncan, Okla.

[73] Assignee: Halliburton Company, Duncan, Okla.

[21] Appl. No.: 359,809

[22] Filed: May 31, 1989

[51] Int. Cl.$^5$ .............................................. B01J 3/04
[52] U.S. Cl. .................................. 422/112; 422/116; 422/242; 417/290; 417/297; 25/129.05
[58] Field of Search ................ 73/863, 863.01, 863.02, 73/863.03, 863.11, 836.12, 863.71, 863.72, 863.73, 864.34, 864.35, 864.51, 865.6, 803.31; 422/242, 112, 116; 137/487.5; 251/63; 129.01-129.22; 417/290, 297.5, 298

[56] References Cited

U.S. PATENT DOCUMENTS

| | | | |
|---|---|---|---|
| 1,357,196 | 10/1920 | Thorssell et al. | 422/242 |
| 2,984,251 | 5/1961 | Quinby | 137/487.5 X |
| 2,986,898 | 6/1961 | Wood, Jr. | 62/174 |
| 3,424,370 | 1/1969 | Law | 230/5 |
| 3,440,256 | 4/1969 | Rich | 422/242 X |
| 3,525,596 | 8/1970 | Grant, Jr. | 422/242 X |
| 3,720,487 | 3/1973 | Wiley | 417/572 |
| 3,729,000 | 4/1973 | Bell | 128/145.6 |
| 3,847,507 | 11/1974 | Sakiyama et al. | 417/22 |
| 3,882,861 | 5/1975 | Kettering et al. | 417/44 X |
| 4,093,404 | 6/1978 | Soehngen et al. | 417/317 |
| 4,158,639 | 6/1979 | Berty | 55/66 X |
| 4,248,268 | 2/1981 | Choate | 138/26 |
| 4,285,639 | 8/1981 | Woodring et al. | 417/218 |
| 4,321,014 | 3/1982 | Eburn, Jr. et al. | 417/5 |
| 4,397,610 | 8/1983 | Krohn | 417/44 |
| 4,430,889 | 2/1984 | Sutton | 73/61.4 |
| 4,559,778 | 12/1985 | Krusche | 417/217 X |
| 4,575,313 | 3/1986 | Rao et al. | 417/26 |
| 4,622,846 | 11/1986 | Moon, Jr. et al. | 73/59 |
| 4,653,313 | 3/1987 | Sabins et al. | 73/61.4 |
| 4,666,374 | 5/1987 | Nelson | 417/46 X |
| 4,917,349 | 4/1990 | Sujaatmodja et al. | 251/63 |

FOREIGN PATENT DOCUMENTS

| | | | |
|---|---|---|---|
| 635560 | 1/1962 | Canada | 137/487.5 |
| 3041045 | 5/1982 | Fed. Rep. of Germany | 422/242 |
| 55-10171 | 1/1980 | Japan . | |
| 9792 | 1/1988 | Japan | 137/487.5 |
| 373707 | 6/1973 | U.S.S.R. | 137/487.5 |
| 1160363 | 6/1985 | U.S.S.R. | 422/242 |
| 958582 | 5/1964 | United Kingdom | 422/242 |

OTHER PUBLICATIONS

PP. 2458 and 2459 of a Halliburton Services brochure dated at least one year prior to May 1989.
Publication entitled "Nowsco News Compact Pressurized Consistometer" dated at least one year prior to May 1989, of Nowsco Well Service Limited.

Primary Examiner—Tom Noland
Attorney, Agent, or Firm—James R. Duzan; Mark E. McBurney; E. Harrison Gilbert, III

[57] ABSTRACT

A pressure control apparatus suitable for controlling pressures in autoclaves permits a plurality of autoclaves to be selectably pressurized from a single pressurizing circuit. The apparatus can be externally controlled to more efficiently multiplex autoclaves to the pressurizing circuit and to more efficiently implement different pressure schedules for the autoclaves. Once a pressure has been set for an autoclave maintained in communication with the main pressurizing circuit, the apparatus automatically monitors the position of the pump piston and resets it from either of its extreme limits of movement to maintain pressure at a desired set point. Corresponding methods are also disclosed.

19 Claims, 15 Drawing Sheets

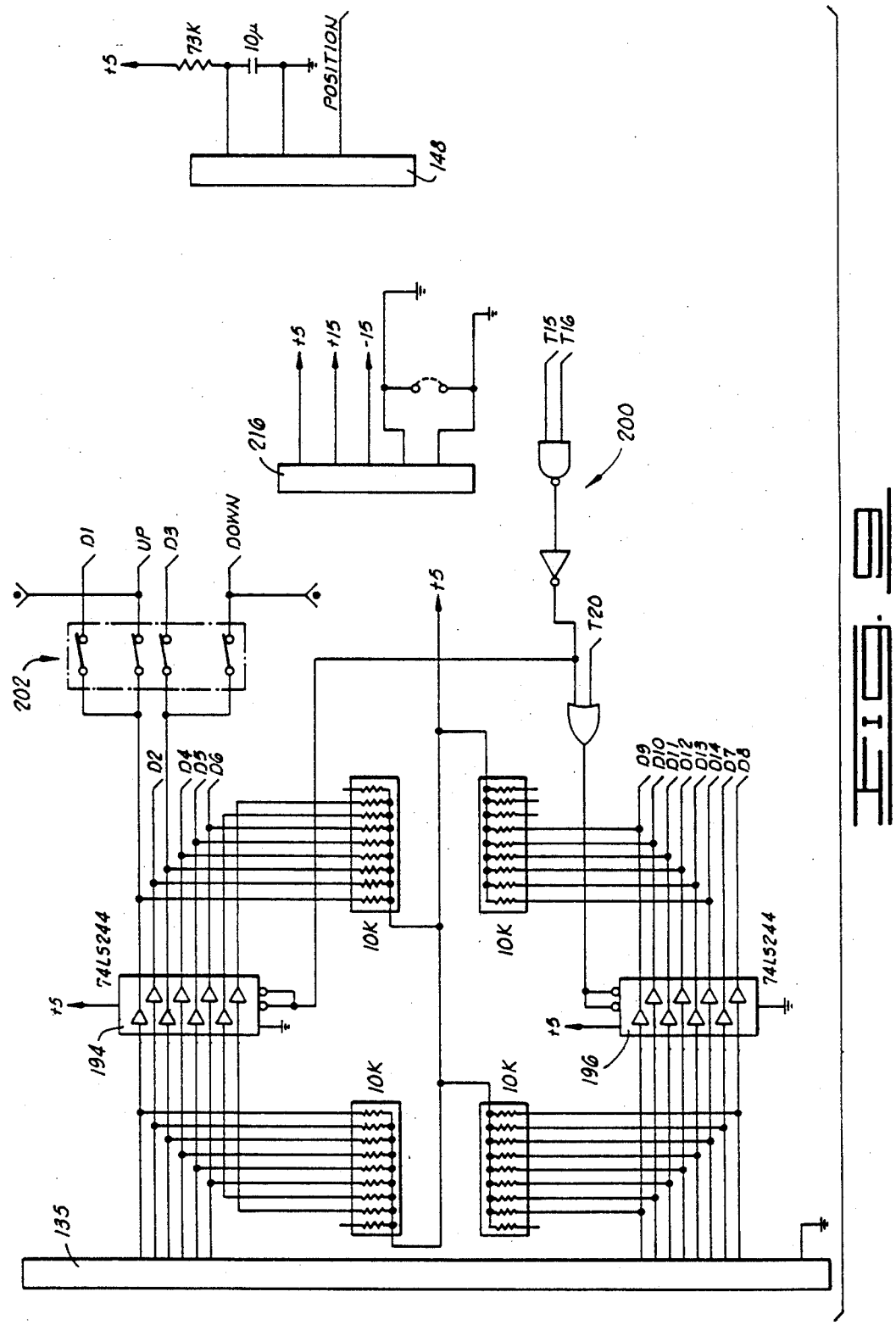

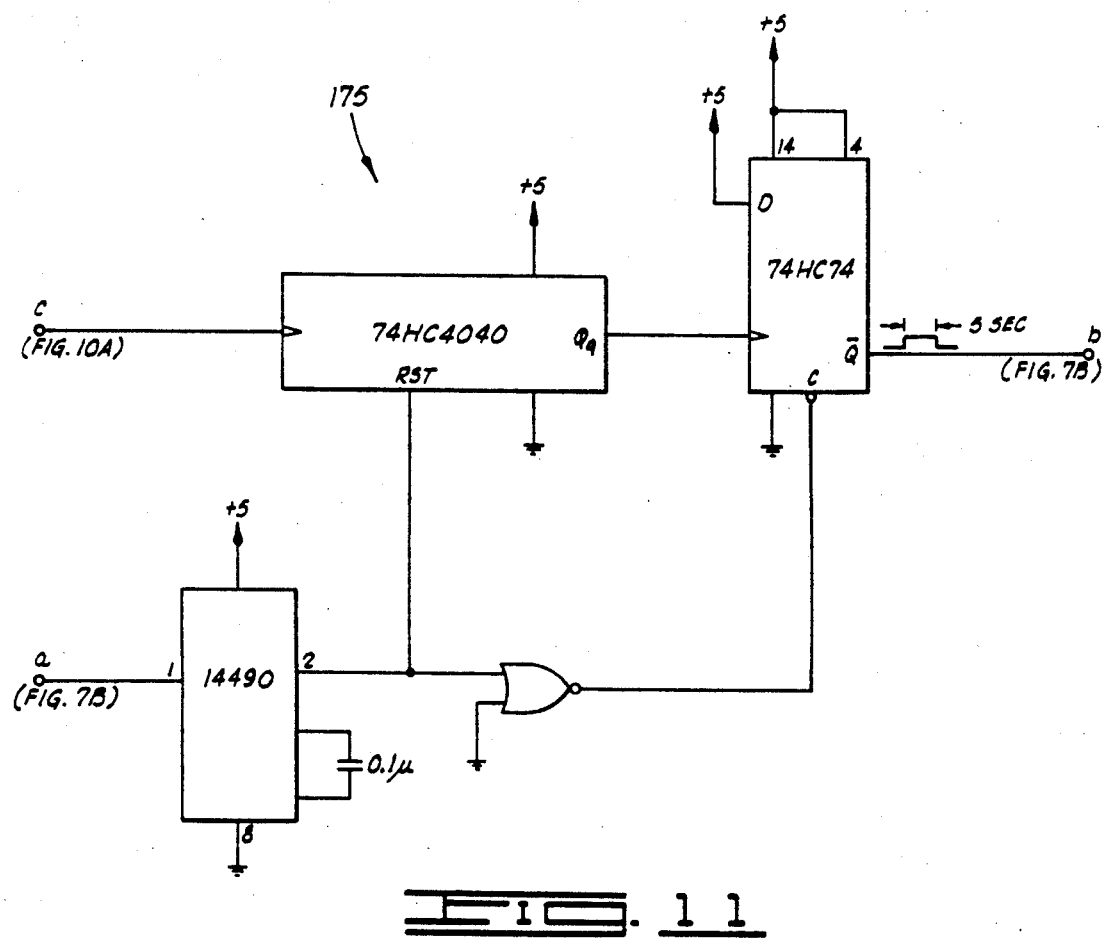

PRESSURE CONTROL APPARATUS AND METHOD

BACKGROUND OF THE INVENTION

This invention relates generally to pressure control apparatus and methods. The invention relates more particularly, but not by way of limitation, to an apparatus and a method for controlling an autoclave valve, a tank valve and a piston of a pump within a fluid circuit for pressurizing an autoclave. The invention also relates more particularly, but not by way of limitation, to an apparatus and method for controlling pressure in a plurality of autoclaves, wherein each autoclave is connected to a respective one of a plurality of valves of a fluid circuit pressurized by a single pump.

In the oil and gas industry, cement slurries are pumped into well bores for various reasons, one of which is for cementing casing. Different well bores can have different temperature and pressure conditions which can affect different cement slurries; therefore, it is desirable to be able to test a particular cement slurry for its suitability for a particular well bore environment. Such testing is well known in the industry.

A typical cement test occurs in a closed container, such as an autoclave, wherein the contents can be maintained under pressure. In at least some applications, heat can also be applied to heat the contents to a desired temperature. The pressure and temperature, when controlled, are typically those anticipated to be encountered downhole. Specific examples of such test equipment are the Halliburton Services Cement Consistometer and the Halliburton Services Ultra-sonic Cement Analyzer (UCA). See also U.S. Pat. No. 4,622,846 to Moon, Jr. et al. and U.S. Pat. No. 4,653,313 to Sabins et al.

To obtain a good test, the pressure (and temperature, if controlled) should be maintained at the desired level. It has been observed, however, that once pressure has been set in an autoclave, for example, the pressure can change over time due to leaks in the system or expansion of the cement under test, for example. There is the need, therefore, for a pressure control apparatus and method by which a desired pressure can be automatically maintained in an autoclave (or other pressure vessel) once it has been established.

In conducting tests of the aforementioned type, it is also sometimes desirable to test multiple samples at the same time. Thus, samples of the same batch of cement could be subjected to different pressures (and temperatures, if desired) to determine how the cement would react to different conditions which might be met in the well bore. Such multiple tests could be run by individual autoclaves and pressurizing equipment; however, it would be more efficient if a number of autoclaves could be pressurized, either to one or more constant levels or in accordance with one or more varying pressure schedules, by a single pressurizing system. That is, there is the need for apparatus and method by which multiple pressure vessels can be multiplexed to a single pressurizing system.

SUMMARY OF THE INVENTION

The present invention overcomes the above-noted and other shortcomings of the prior art and meets the aforementioned needs by providing a novel and improved pressure control apparatus and a novel and improved pressure control method. By the apparatus and method of the present invention, a selected pressure can be automatically maintained in an autoclave or other pressurizable chamber and a plurality of such chambers can be pressurized in a multiplexed manner from a single pressurizing system.

An advantage of a preferred embodiment of the present invention particularly adapted for controlling autoclaves in which cement samples can be tested is that it can be operated under manual or computer control. Under manual control, the invention will maintain pressure to a predetermined level without operator interaction, thereby automatically compensating for fluid expansions, leakage, etc. Multiplexing is more efficiently performed under computer control, because each channel can thereby be automatically controlled according to different pressure schedules if desired. In either manual or computer mode, the invention will refill or discharge fluids from the pressurized chamber when it becomes necessary. This is performed in a sequential manner so that there is no substantial loss or increase of pressure during the corrective operation. In a particular implementation, the invention controls up to eight channels, each of which has a high pressure air operated autoclave valve and is pressurized in response to operation of a piston type intensifier pump. With the piston type intensifier pump, the invention will continuously report the position of the pump so that with this information, and the pressure change resulting from a piston position change, the relative compressability of the cement can be determined.

For maintaining pressure, the present invention provides an automatic pressure control apparatus, comprising: a pump including a chamber defined therein and further including a piston disposed in the chamber so that the piston is movable between a first limit position and a second limit position; a first valve; first valve operating means, connected to the first valve, for opening and closing the first valve; a second valve; second valve operating means, connected to the second valve, for opening and closing the second valve; fluid conducting means for connecting the chamber of the pump and the first and second valves; detector means, connected to the pump, for generating a signal in correspondence with the position of the piston within the pump; means, connected to the detector means, for providing a first limit position signal in response to the signal of the detector means corresponding to the piston having moved to the first limit position; means, connected to the detector means, for providing a second limit position signal in response to the signal of the detector means corresponding to the piston having moved to the second limit position; first control means, connected to the means for providing a first limit position signal and to the means for providing a second limit position signal, for controlling the first valve operating means to close the first valve in response to either the first limit position signal or the second limit position signal; second control means, connected to the means for providing a first limit position signal and to the means for providing a second limit position signal, for controlling the second valve operating means to open the second valve in response to either the first limit position signal or the second limit position signal; means, connected to the means for providing a first limit position signal and to the means for providing a second limit position signal, for moving the piston away from the first or second limit position in response to the respective one of the first or second limit position signal; and means, connected to the detector means, for operating the second control means and the first control means to control the second valve operating means and the first valve operating means, respectively, to close the second valve and to open the first valve, respectively, in response to the signal of the detector means corresponding to the piston having moved away from the first and second limit positions.

The present invention provides a corresponding method. In a preferred embodiment, the present invention provides a method of controlling pressure in an autoclave, comprising: connecting an autoclave to a first valve of a fluid circuit, which fluid circuit further includes a second valve through which a fluid source communicates with the fluid circuit and which fluid circuit also includes a piston movable between first and second positions within the fluid circuit; pressurizing the fluid circuit and the autoclave to a selected pressure with fluid from the fluid source, including controlling the first valve, the second valve and the piston so that when the selected pressure is obtained, the first valve is open, the second valve is closed and the piston is not at either the first position or the second position; and automatically detecting, through an electrical circuit responsive to the position of the piston, if the piston moves to either the first position or the second position and thereupon automatically through the electrical circuit sequentially closing the first valve, opening the second valve, moving the piston to a predetermined position between the first and second positions, closing the second valve, and opening the first valve.

Regarding the control of the pressures of a plurality of autoclaves, the present invention provides a pressure control apparatus, comprising: a pump; a plurality of valves, each of the valves dedicated for connecting to a respective autoclave; fluid conducting means for connecting the pump and the valves; pressure control means, connected to the pump, for controlling the pump to provide a selected pressure within the fluid conducting means; and valve control means, connected to the valves, for selectably controlling the valves so that a selected valve can be opened to communicate a selected pressure provided in the fluid conducting means to an autoclave connected to the selected valve.

The present invention provides a method corresponding to the functions implemented by the foregoing apparatus. In a preferred embodiment, the present invention provides a method of controlling pressure in a plurality of autoclaves, each autoclave connected to a respective one of a plurality of valves of a fluid circuit, which fluid circuit further includes a pump connected to the valves, which method comprises: a) operating the pump to pressurize the fluid circuit to a selected pressure; b) opening and closing at least one valve to communicate the selected pressure to the autoclave connected thereto; and c) repeating steps a) and b) until selected autoclaves are pressurized to respective selected pressures in response to operation of the pump.

Therefore, from the foregoing, it is a general object of the present invention to provide a novel and improved pressure control apparatus and a novel and improved pressure control method. Other and further objects, features and advantages of the present invention will be readily apparent to those skilled in the art when the following description of the preferred embodiment is read in conjunction with the accompanying drawings.

BRIEF DESCRIPTION OF THE DRAWINGS

FIG. 9 shows a schematic circuit diagram of input circuitry for receiving into the preferred embodiment apparatus data signals from an external controller such as a computer.

FIG. 11 shows a schematic circuit diagram of a preferred alternate embodiment of a timer shown in FIG. 7B.

DETAILED DESCRIPTION OF PREFERRED EMBODIMENT

Figure 2:
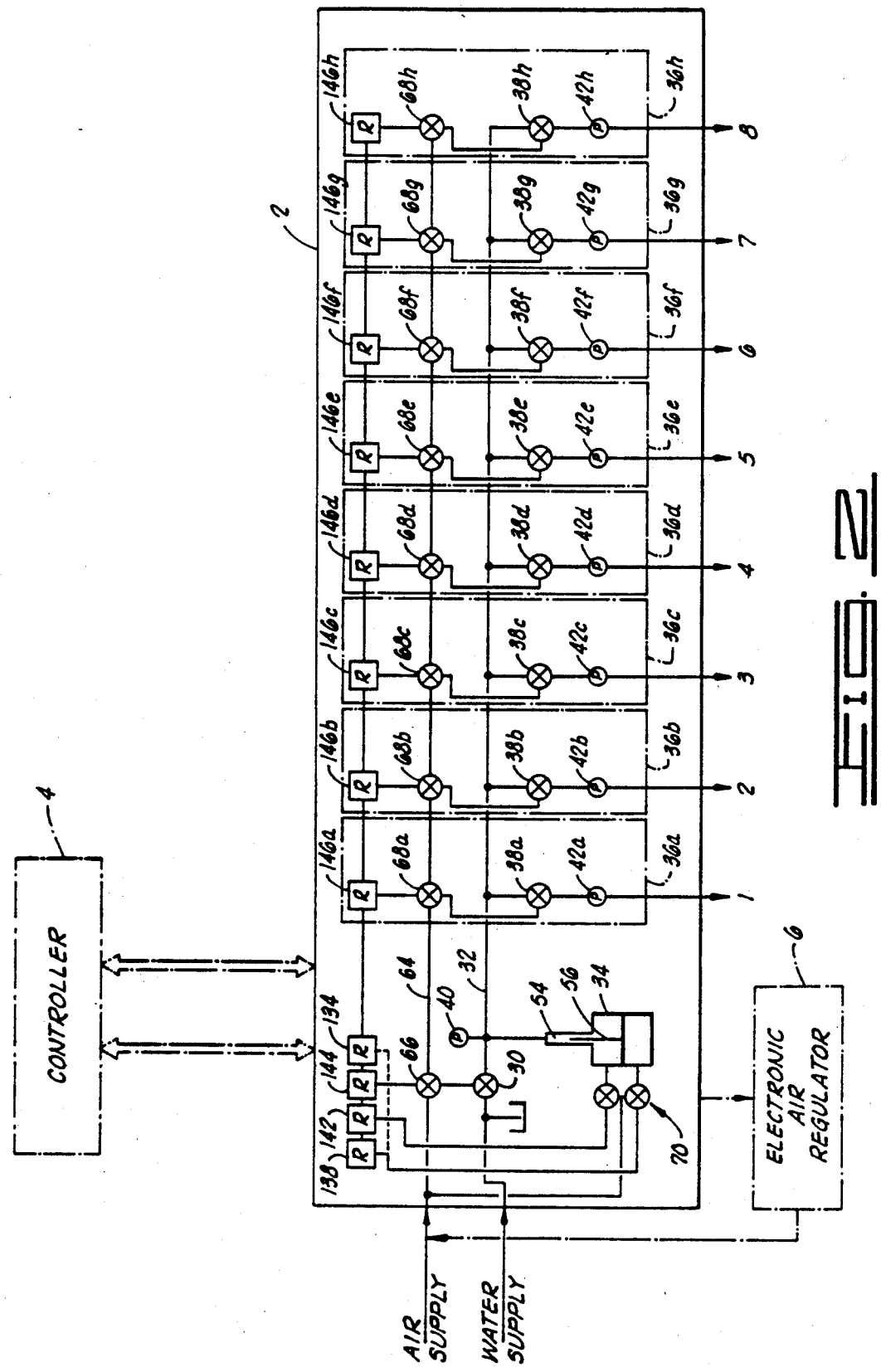
FIG. 2 shows a schematic diagram of pressurizing and control fluid circuits contained in the housing of the preferred embodiment apparatus.

The preferred embodiment of the present invention is contained within a housing 2 schematically shown in FIG. 2. Although the preferred embodiment to be described hereinbelow is contained in the housing 2, there are external devices which can be added to or used with the components contained within the housing 2. These include a controller 4, such as a conventional microcomputer programmed to interact in a manner which will become apparent from the further description herein of the invention. Another example of an external device which can be used with the preferred embodiment of the present invention is a conventional electronic air regulator 6.

Figure 1:
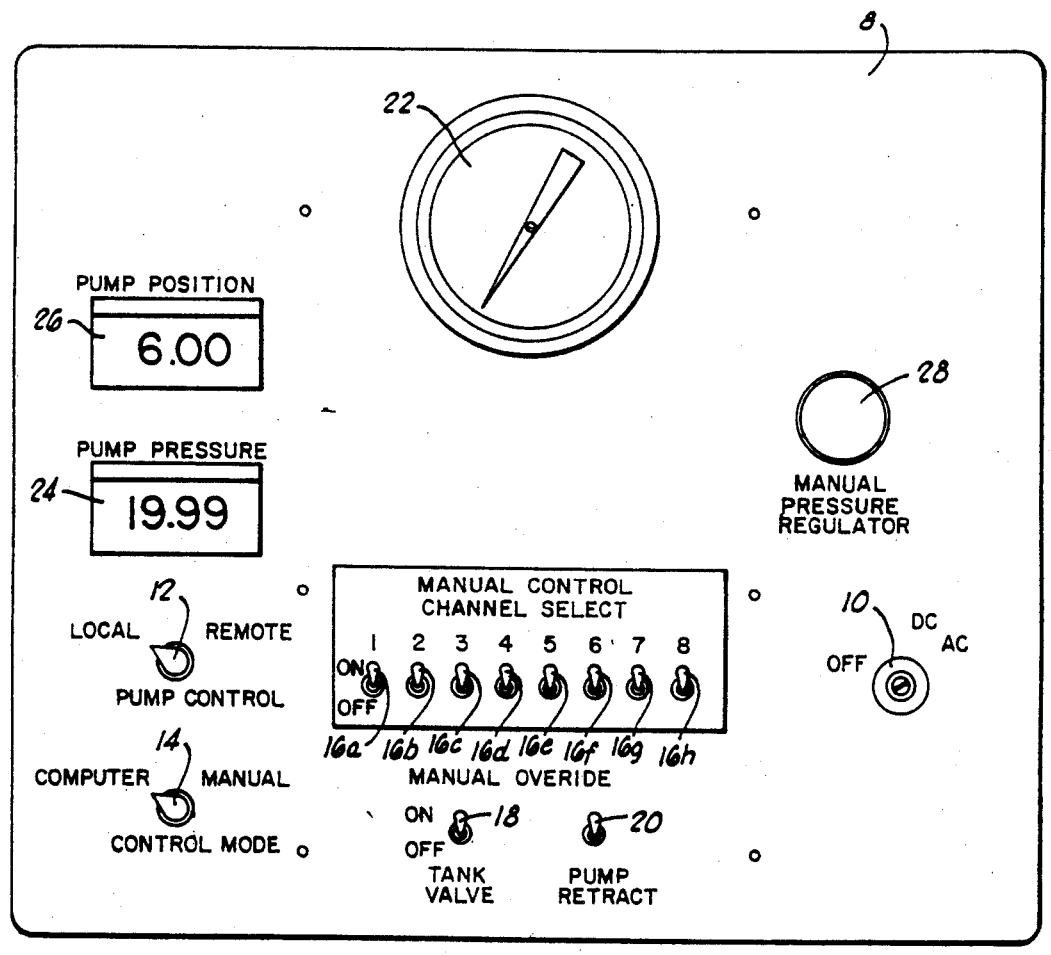
FIG. 1 shows an elevational view of a front panel of a housing of the preferred embodiment apparatus of the present invention.

The housing 2 of the preferred embodiment includes a front panel 8 shown in FIG. 1. Accessible on the front panel 8 are the following items which are implemented by conventional equipment: power on/off switch 10, which is switchable among an off position, a "dc" position wherein the internal circuits except for valve-actuating relays subsequently described are energized, and an "ac" position wherein all the internal circuits are energized; a local/remote switch 12, which is switchable between a "local" position wherein a pump contained within the housing 2 is automatically controlled by internal circuitry and a "remote" position wherein the pump is not automatically controlled by the internal circuitry but can be controlled by the external controller 4; a computer/manual switch 14, which is switchable between a "computer" position wherein the controller 4 can control a single pressurizing circuit within the housing 2 and multiplex to the pressurizing circuit pressure vessels connected to couplings of the housing 2 and a "manual" position wherein pressure setting and pressure vessel pressurizing are controlled through the components of the front panel 8; a plurality of channel select switches 16 (specifically eight, 16a–16h, in the illustrated embodiment) by which the plurality of individual channels (and the respective connected pressure vessels) to be controlled by the present invention are manually selected; manual override switches, including a tank valve switch 18 and a pump retract switch 20 which can be manually operated to control directly a tank valve and a pump retract valve, respectively, to be described hereinbelow; an analog pressure gauge 22 and a digital pressure display 24, both of which are for displaying the system pressure of the pressurizing circuit contained within the housing 2 (in the preferred embodiment, the display 24 functions only in response to the controller 4); a digital display 26 for displaying the position of a piston of the pump contained within the housing 2; and a pressure regulator manual control knob 28 by which a pressure regulator within the housing 2 can be manually controlled. The fluid systems controlled by the foregoing are generally depicted in FIG. 2 and more specifically shown in FIGS. 3–5. The electrical systems controlled by the foregoing are illustrated in FIGS. 6–11.

The fluid systems generally depicted in FIG. 2 include a pressurizing fluid system and a control fluid system. The pressurizing fluid system can be pressurized to a suitable high pressure dependent upon specific equipment used, and the control fluid system is a lower pressure system providing air or other suitable fluid to operate high pressure valves within the pressurizing fluid system, for example.

Referring to FIG. 2, the pressurizing fluid system, or circuit, includes a tank valve 30 connected by a fluid conducting means 32 to a pump 34 and a plurality of channels 36 (eight channels 36a–36h are illustrated) through which the chambers of autoclaves or other pressure vessels (not shown) can be connected for being pressurized by the pump 34. In each of the channels 36 there is a corresponding valve 38. Located within the fluid conducting means 32 between the valves 30, 38 for monitoring the main system pressure is a pressure transducer 40, and located in each of the channels 36 between the respective valve 38 and a respective coupling for the external pressure vessel is a respective pressure transducer 42.

The tank valve 30 is the main flow valve means for communicating a source of fluid for pressurizing the circuit with the fluid conducting means 32. The valves 38a–38h are the valves by which individually connected pressure vessels are communicated with the pressure within the fluid conducting means 32. Each valve 38 is dedicated for connecting to a respective pressure vessel. The valves 30, 38 can be conventional high pressure valves known in the art; however, in the preferred embodiment the preferred valve is the high pressure valve disclosed in U.S. Pat. Application Ser. No. 329,930, filed Mar. 29, 1989, now U.S. Pat. No. 4,917,349 and assigned to the assignee of the present invention.

Figure 3:
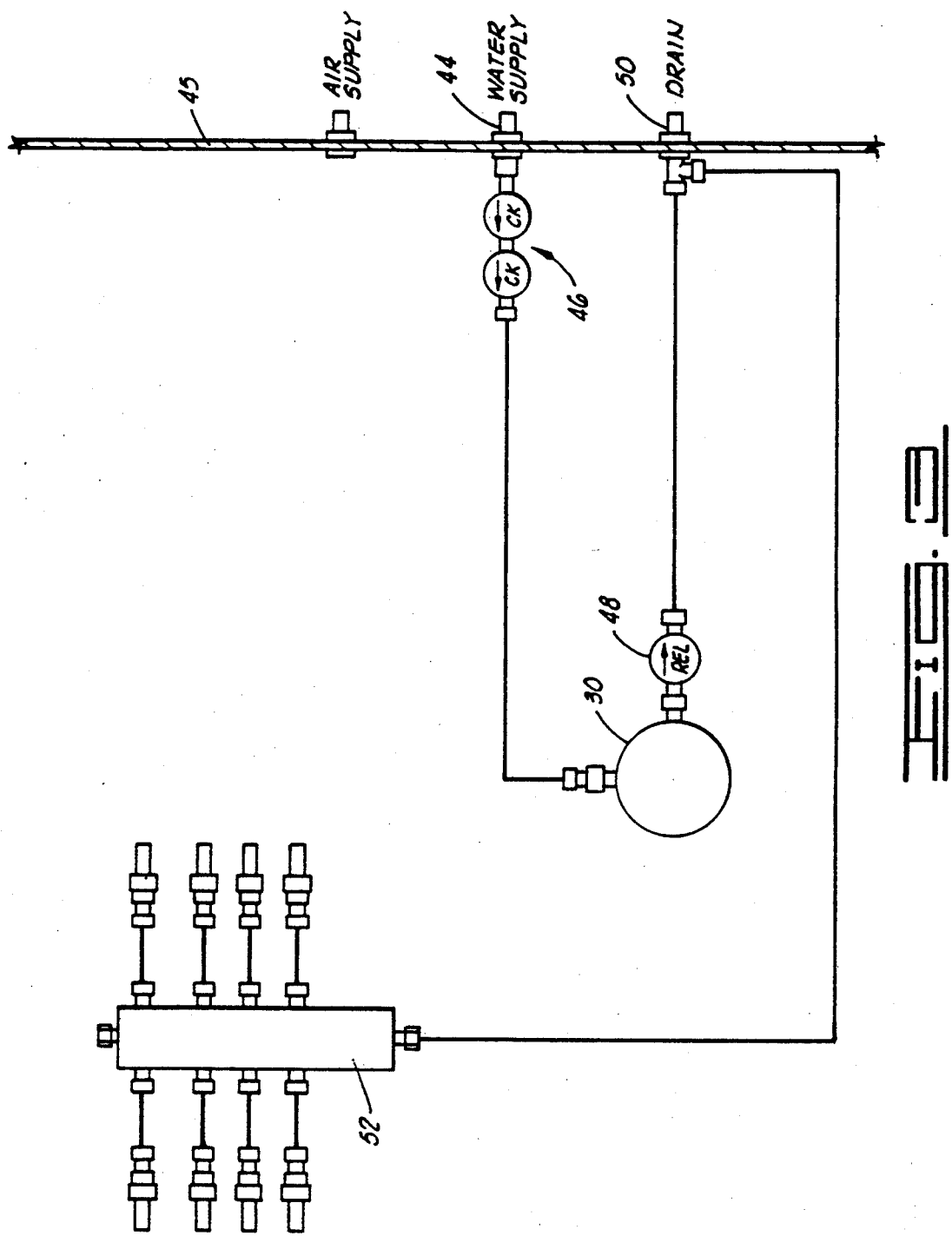
FIG. 3 depicts a particular implementation of a tank valve and its inlet and drain connections of the pressurizing fluid circuit of the preferred embodiment apparatus.

Particular connections for the tank valve 30 in the preferred embodiment are shown in FIG. 3. The tank valve 30 receives an inlet flow from a suitable source of fluid to be used in pressurizing the system. One suitable fluid source is the municipal water supply. This is input through a coupling 44 on a back panel 45 of the housing 2. The inlet flow comes in from the coupling 44 through check valves 46 connected to the tank valve 30. A relief valve 48 is connected to the tank valve 30 to vent fluid to an external drain connectable at a coupling 50 on the back panel 45 and to a drain accumulator 52 inside the housing 2.

Referring to FIG. 2, the fluid conducting means 32 is conventional tubing suitable for conducting fluid, such as water, and for withstanding the pressure exerted through operation of the pump 34.

The pump 34 is a small, but conventional pressurizing or intensifier pump which is mounted within the housing 2. The pump 34 includes a chamber 54 in which a piston 56 is movable between two limit positions which, for the orientation shown in FIG. 2, can be referred to as an upper limit position and a lower limit position which are the extremes to which the piston 56 can move within the pump 34. The chamber 54 is connected to the fluid conducting means 32 in a known manner.

Figure 4:
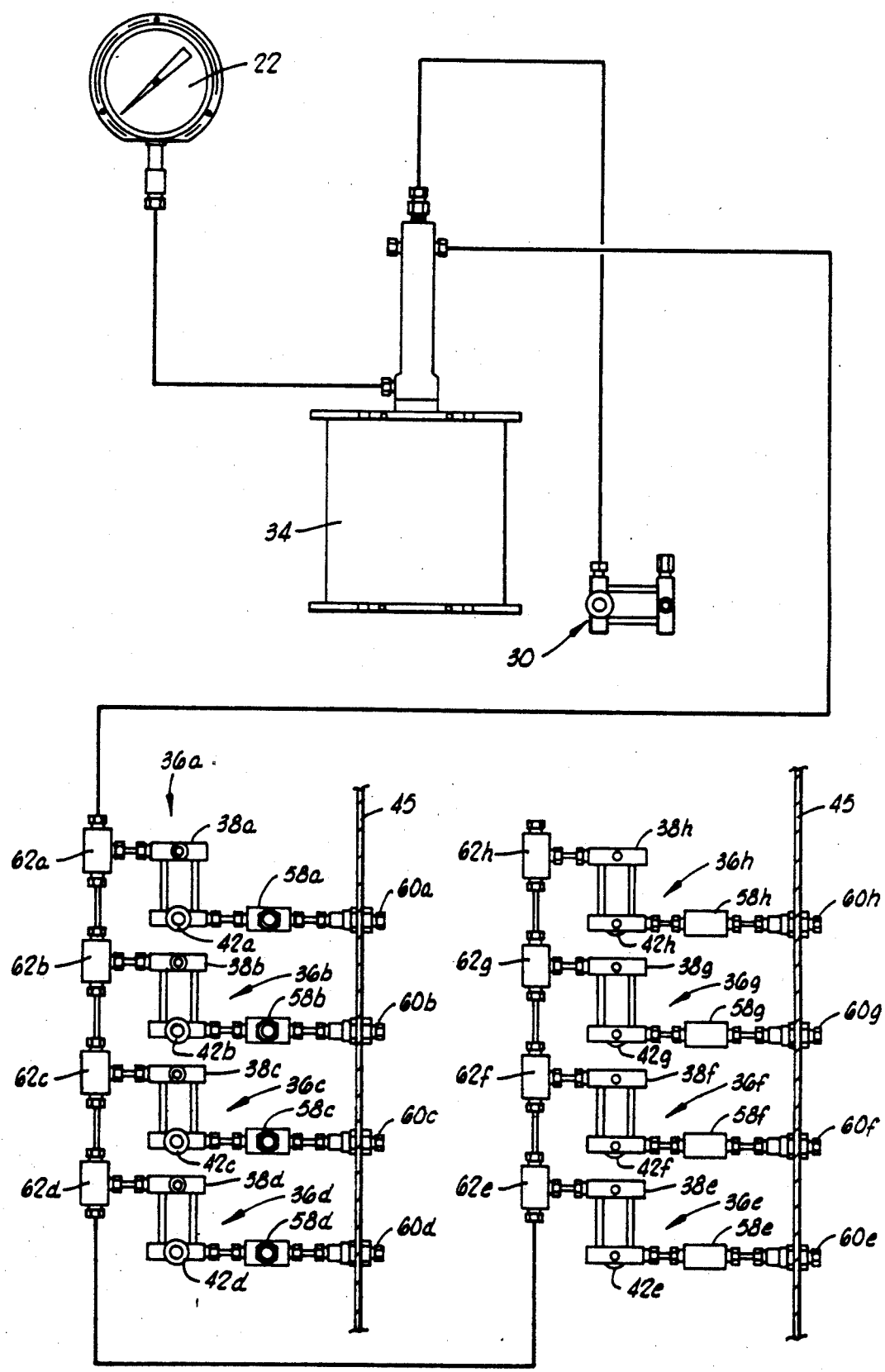
FIG. 4 depicts a particular implementation of the rest of the pressurizing fluid circuit of the preferred embodiment apparatus.
Figure 5A:
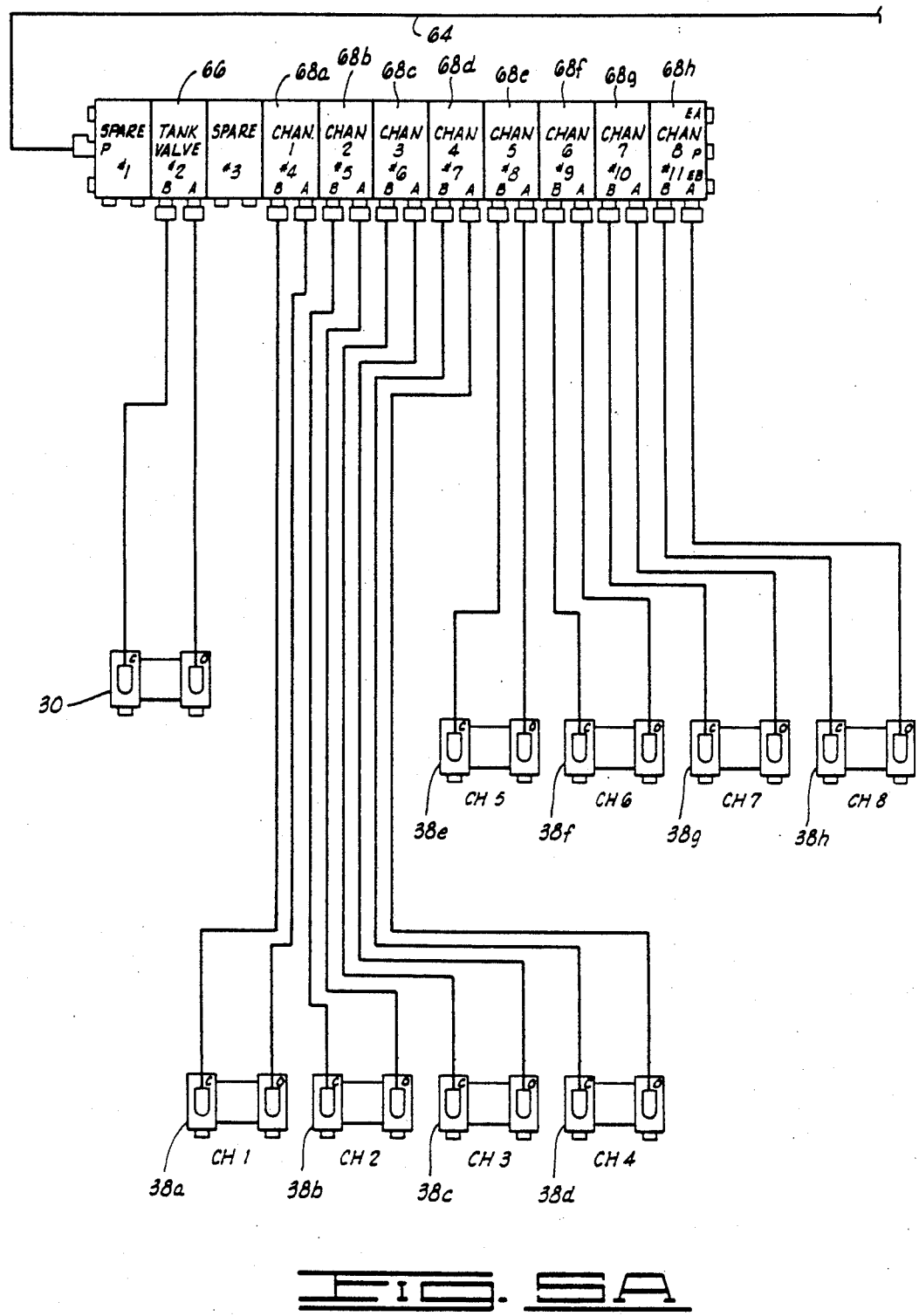
FIGS. 5A–5B depict a particular implementation of the control fluid circuit of the preferred embodiment apparatus.

The pressurizing fluid system or circuit of the preferred embodiment is more particularly illustrated in FIG. 4. Safety rupture disks 58a–58h are shown connected between respective valves 38a–38h and respective external couplings 60a–60h mounted on the back panel 45 of the housing 2 for receiving connections from the autoclaves or other devices to be pressurized. Channels 36a–36h branch from the main line of the fluid conducting means 32 at respective conventional T-connectors 62a1–62h. The other elements of FIG. 4 correspond to the elements marked with the same reference numerals in FIG. 2.

Another fluid system of the preferred embodiment of the present invention shown in FIG. 2 is the low pressure, or control, fluid system. Referring to FIG. 2, this includes fluid conducting means 64, such as conventional tubing suitable for conducting low pressure air, into which sole valves 66 and 68a–68h are connected. The low pressure or control fluid system also includes solenoid valves 70. This system is more particularly shown in FIGS. 5A–5B.

Figure 5B:
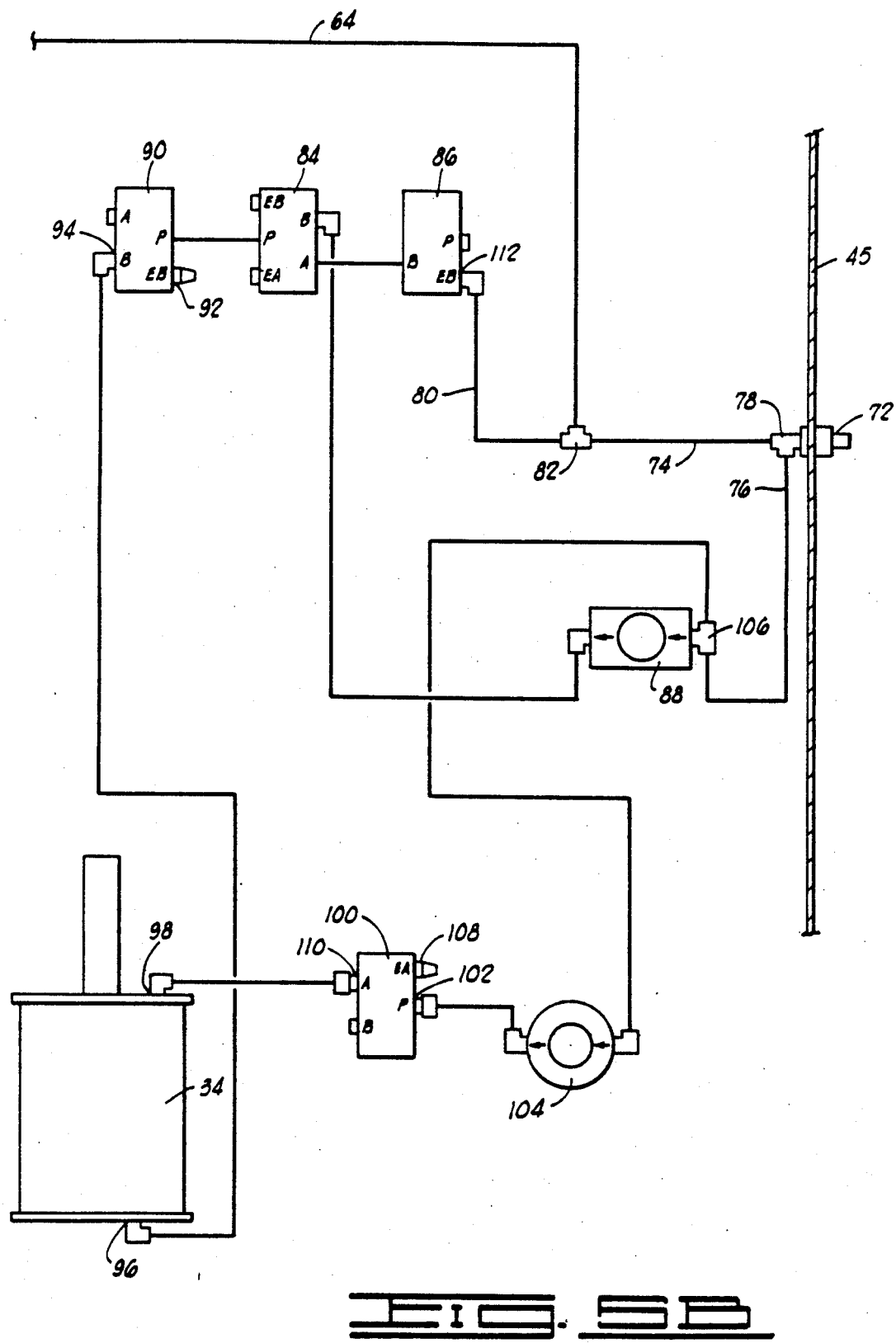

Referring to FIG. 5B, an air supply inlet coupling 72 is mounted on the back panel 45 of the housing 2. An air conducting line 74 and an air conducting line 76 branch from a T-connector 78 connected to the coupling 72. From the line 74, the fluid conducting means 64 and a line 80 branch at a T-connector 82. The fluid conducting means 64 provides air to the solenoid valves 66, 68a–68h to which the respective high pressure valves 30, 38a–38h are connected. As will be described further hereinbelow, each of the solenoid valves 66, 68a–68h is controlled to provide air to either close or open the respective high pressure valve. This is apparent from the circuitry shown in FIG. 5A.

Part of the control fluid system shown in FIG. 5B is a pump operating circuit which is generally identified in FIG. 2 by the valves 70. This includes a main control valve 84 into which air is input through a computer-controlled valve 86 and an air regulator 88 controlled by the knob 28 mounted on the front panel 8 shown in FIG. 1. Air from either the valve 86 or from the air regulator 88 is provided through the valve 84 to a valve 90 having an exhaust outlet 92 and a control port 94 connected to an "up" port 96 of the pump 34. Connected to a "down" port 98 of the pump 34 is a pump retract valve 100 having an inlet 102 connected through a lubricator 104 to the air supply inlet coupling 72 through a T-connector 106 having another branch connected to the inlet of the air regulator 88. The pump retract valve 100 has an exhaust outlet 108 and a control port 110.

For the illustrated preferred embodiment, the pump control valves 84, 90, 100 are included within the pump control means for communicating a pump driving fluid, namely air in the preferred embodiment, to the pump 34. Pressurized air input through the valves 84, 90 acts to move the piston up for the orientation shown in FIG. 5, and pressurized air input through the valve 100 acts to move the piston down for the same orientation. The particular setting of the piston 56 within the pump 34 is established by the air pressure applied through these valves, particularly the adjustable air pressures applied through the valves 84, 90.

One adjustable air pressure which can be switched through the valve 84 is manually selected by manually setting the air regulator 88 via the control knob 28. Another adjustable air pressure which can be switched through the valve 84 is provided via a means which is responsive to control from a computer. This means includes: the inlet valve 86 whose input 112 is adapted for receiving a pressure which is controlled by an external conventional electronic air regulator; means for operating the inlet valve 86 in response to control from the computer, which valve 86 operating means includes the combinational logic and relay circuit 114 shown in FIG. 8 and more particularly described hereinbelow; and means for controlling the electronic air regulator in response to control from the computer, which electronic air regulator control means includes the circuits shown in FIG. 10, which will be more particularly described hereinbelow.

The pump control means further includes switch means for selecting which of the two pressurized air sources is passed by the pump control valves. In the preferred embodiment, this switch means includes the computer/manual switch 14 which controls the valve 84. When the switch 14 is in the "computer" position, the valve 84 connects the air pressure from the valve 86 to the inlet of the valve 90; and when the switch 14 is in the "manual" position, the manually controlled pressure from the air regulator 88 is communicated through the valve 84 to the inlet of the valve 90.

The means by which the valves 84, 90, 100 are controlled will be more particularly described hereinbelow with reference to the electrical system of the present invention.

The electrical system of the preferred embodiment of the present invention will next be described with reference to FIGS. 6-11. Within this system are means for controlling the various valves which include the solenoid valves 66, 68 and the valves 86, 90, 100 by which the pump 34 is controlled (the valve 84 has already been described as being controlled by the switch 14).

Figure 6A:
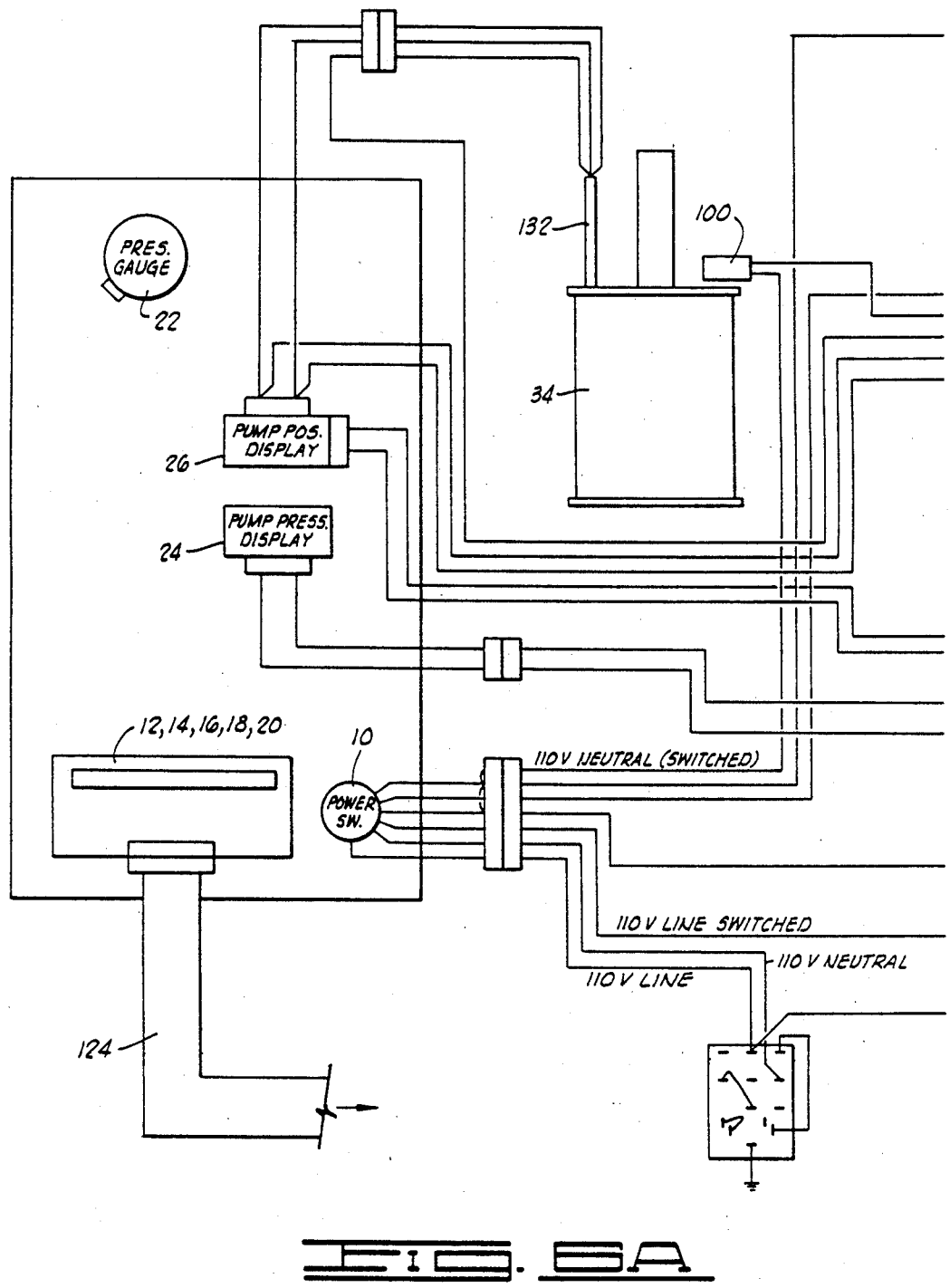
FIGS. 6A–6B show a schematic wiring diagram of electrical components within the housing of the preferred embodiment apparatus.
Figure 6B:
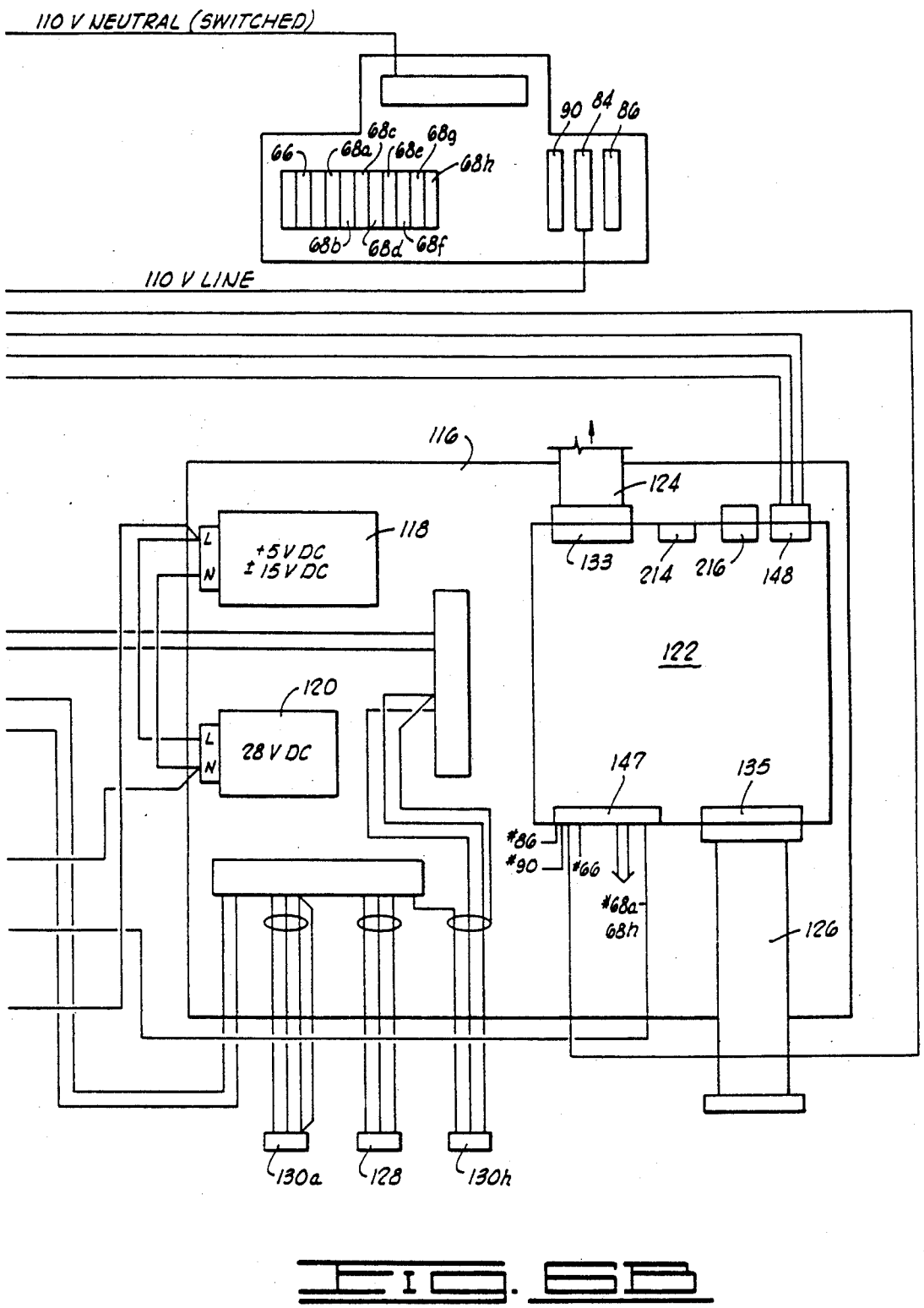

Referring to FIGS. 6A-6B, the electrical system is primarily mounted on a panel 116 (FIG. 6B) contained within the housing 2. The panel 116 contains conventional voltage regulators 118, 120. The panel 116 also contains circuits 122 more particularly shown in FIGS. 7-11. The circuits 122 are connected to the front panel switches 12, 14, 16, 18, 20 through a ribbon cable 124. The circuits 122 are connectable to the external controller 4, such as a microcomputer, through a ribbon cable 126. Other connectors of the circuits 122 are shown in FIG. 6B; the details of these connectors will become apparent from the subsequent description of the remaining drawings.

The panel 116 also has connectors 128 and 130a–130h (connectors 130b–130g not shown to simplify the drawing). The connector 128 is used to provide the signal from the main pressure transducer 40 to the external controller 4 (if used), and the connectors 130a–130h are used to connect the individual channel pressure transducers 42a–42h to the external controller 4 (if used).

The remainder of the wiring diagram shown in FIG. 6 is believed to be self-explanatory in that the remaining elements correspond to previously described elements as indicated by the use of like reference numerals, except for a linear potentiometer 132 which is used to detect the position of the piston 56 within the pump 34 in a known manner. The output of the linear potentiometer 132 is provided to the circuits 122 as shown in FIGS. 6A–6B.

Figure 7A:
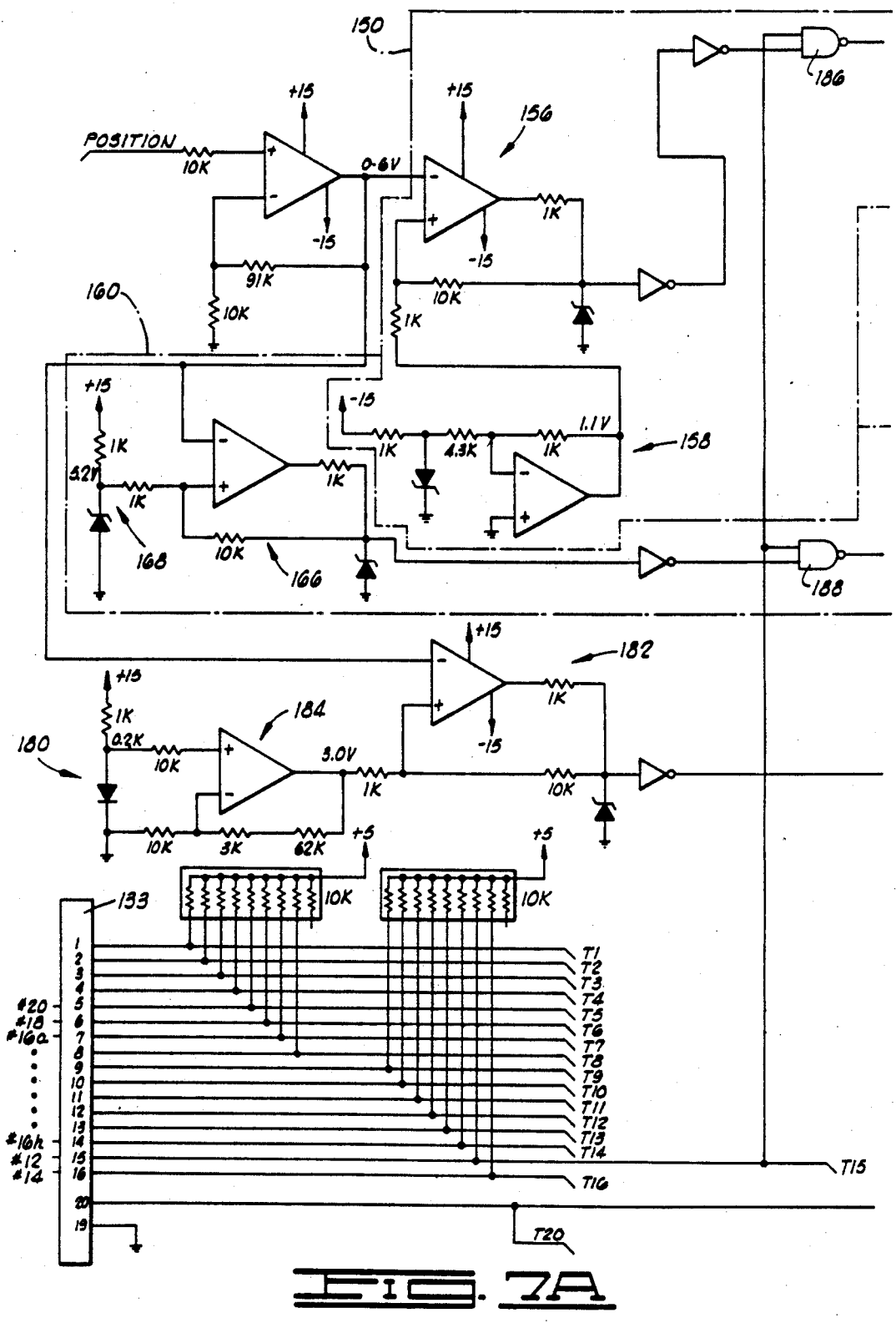
FIGS. 7A–7B show a schematic circuit diagram of electrical control circuits of the preferred embodiment apparatus.

The signal from the linear potentiometer 132 is identified in FIG. 7A as the "position" signal. As also shown in FIG. 7A, the manual front panel switches 20, 18, 16a–16h, 12, 14 are connected through the cable 124 to provide control signals T5, T6, T7–T14, T15, T16, respectively through a connector 133. Fourteen control signals, D1–D14, can be provided to the circuits 122 from the external controller 4 through the cable 126 connected to a connector 135 identified in FIG. 9. These signals, T5–T16 and D1–D14, can be used to control a plurality of valve actuating means which include relays 134, 136, 138, 140, 142, 144, 146a–146h shown in FIG. 8.

Figure 8:
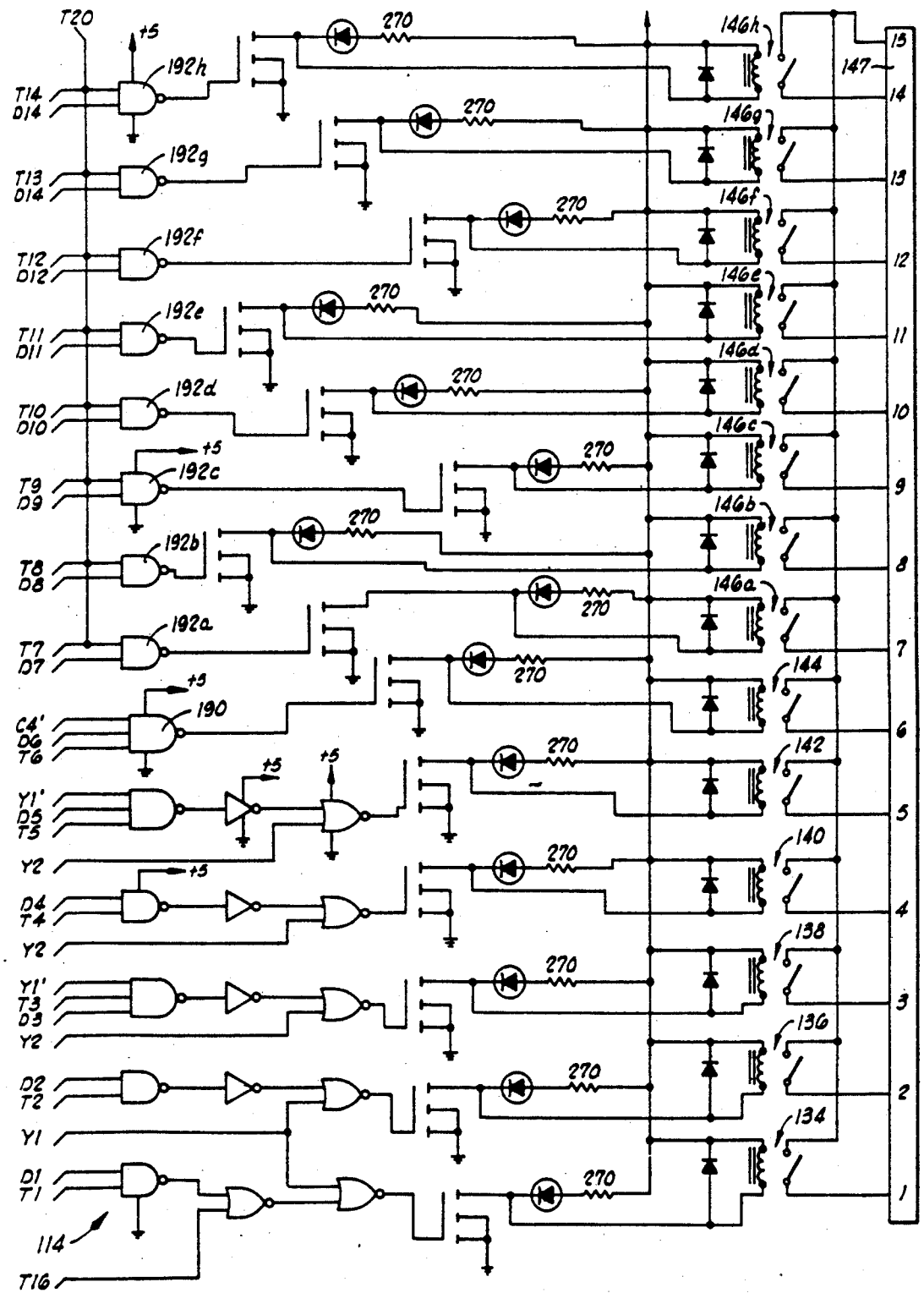
FIG. 8 shows a schematic circuit diagram of relays and associated combinational logic by which valves of the control fluid circuits are operated in the preferred embodiment apparatus.
Figure 10A:
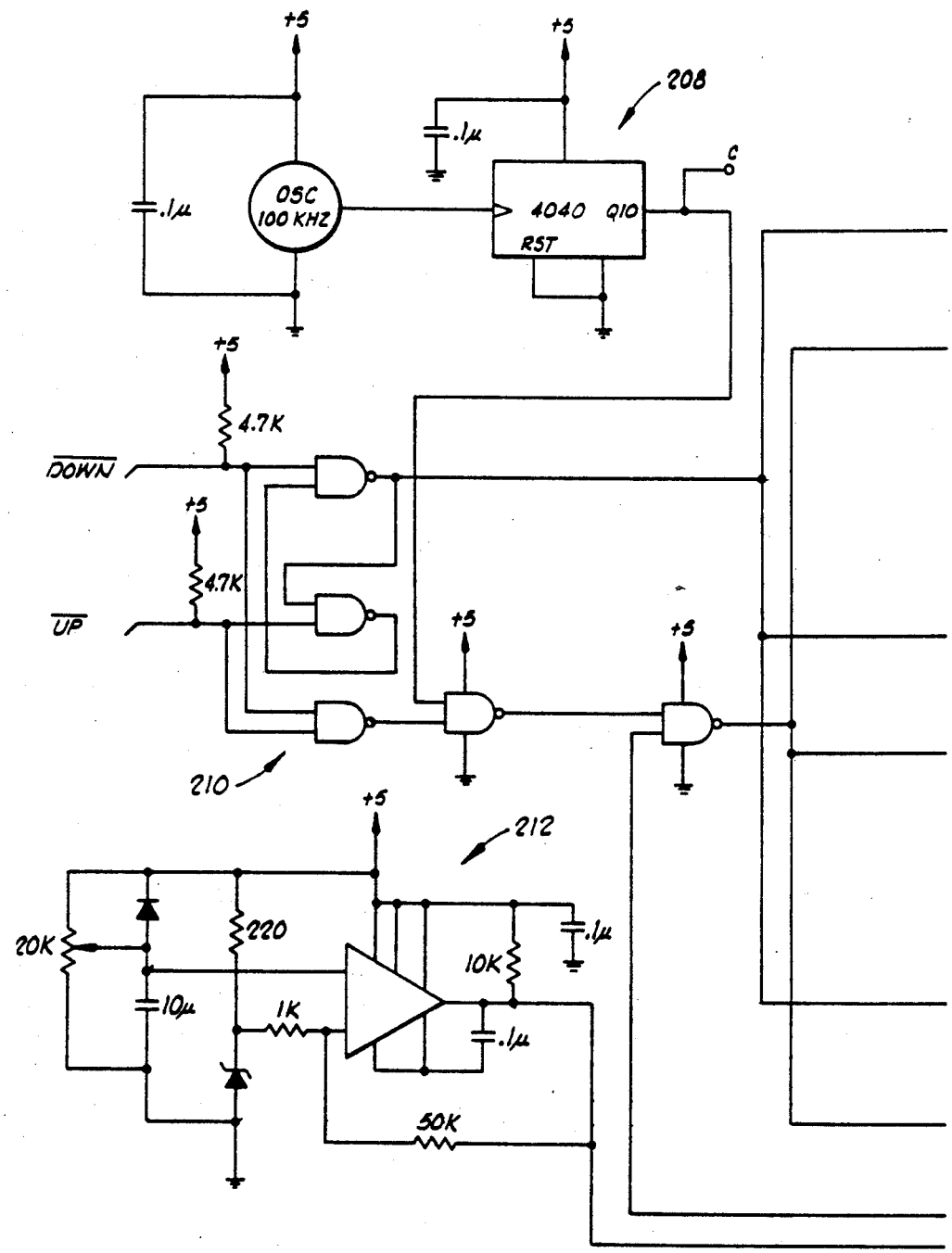
FIGS. 10A–10B show a schematic circuit diagram of a circuit for controlling from the preferred embodiment apparatus an external electronic actuating fluid (e.g.,air) regulator.
Figure 10B:
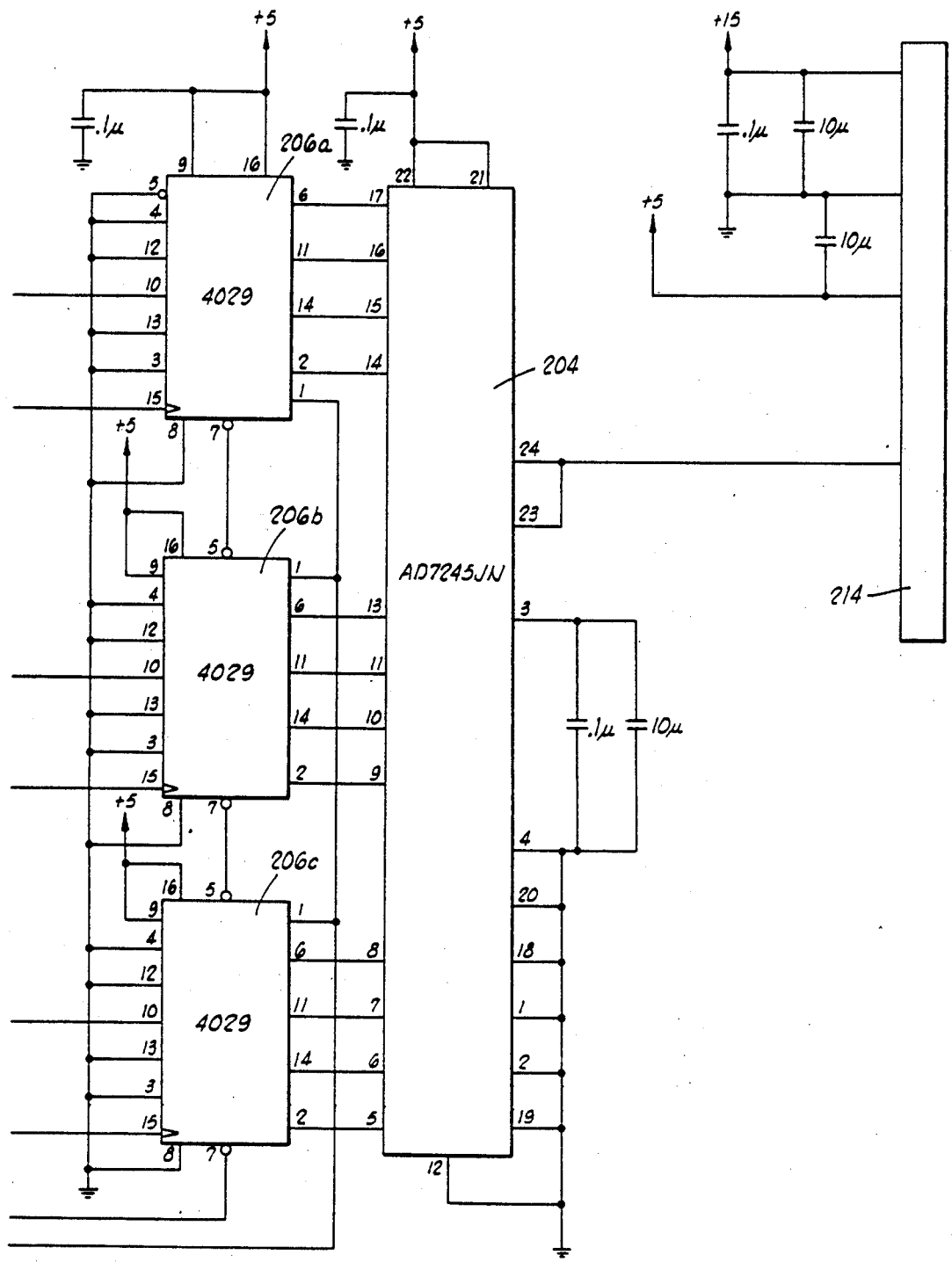

The relay 134 operates the valve 86; the relay 136 is not used in the preferred embodiment; the relay 138 operates the valve 90; the relay 140 is not used in the preferred embodiment; the relay 142 operates the retract valve 100; the relay 144 operates the solenoid valve 66 which in turn operates the tank valve 30; the relays 146a–146h operate the solenoid valves 68a–68h, respectively, which in turn operate the individual channel valves 38a–38h, respectively. Connections between these relays and valves are made through a connector 147. The uppermost connection to the connector 147 shown in FIG. 8 is the switched 110 VAC line which is energized only when the on/off switch 10 on the front panel 8 is in the "AC" position.

The relay 144 and the solenoid valve 66 define a valve operating means for opening and closing the main flow valve 30, and each relay 146 and its respective solenoid valve 68 define valve operating means for opening and closing the respective valve 38. These operating means and the other relays shown in FIG. 8 are controlled through the circuits shown in FIGS. 7A, 7B and 8.

Figure 7B:
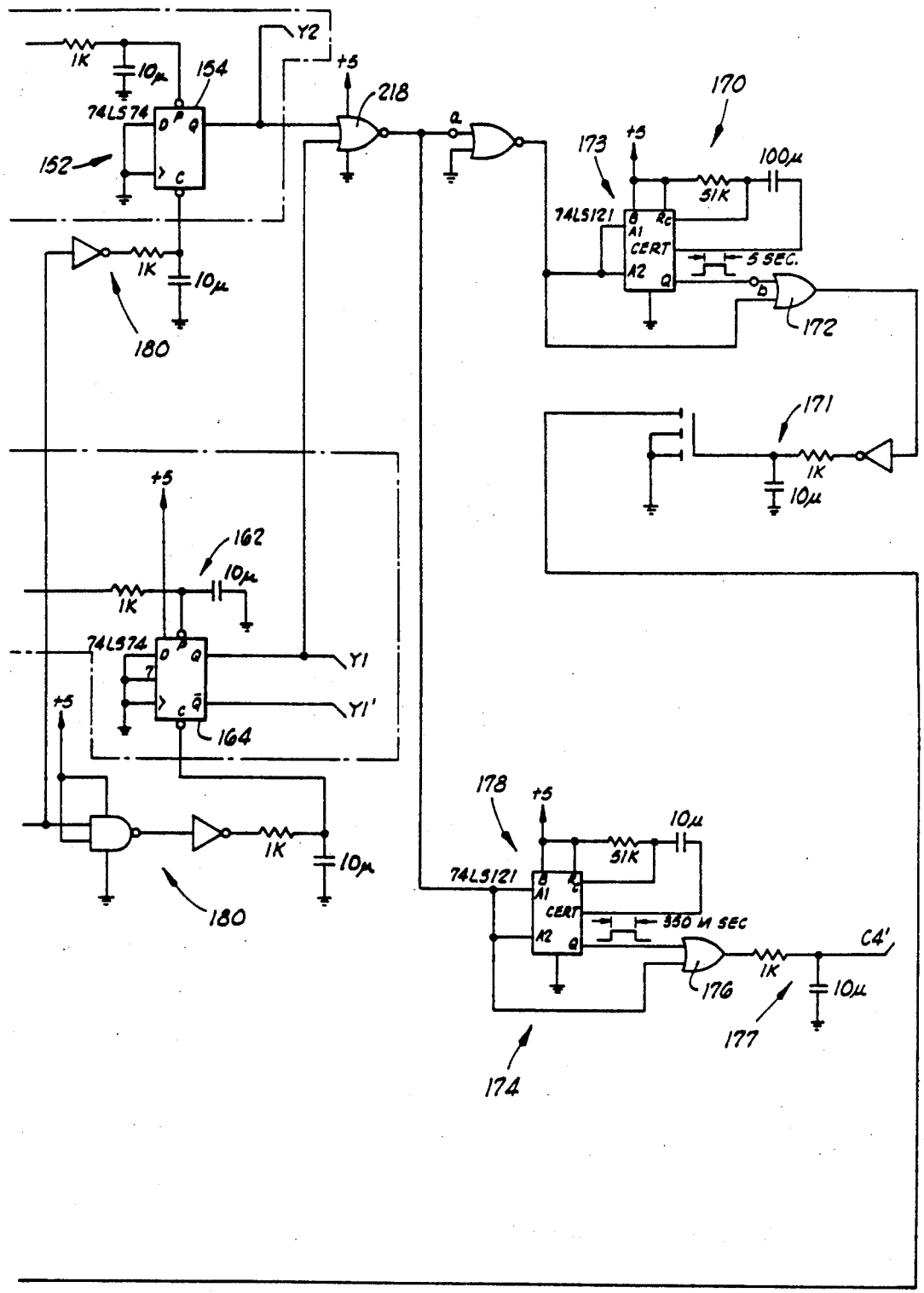

The circuits shown in FIGS. 7A–7B are responsive to the "position" signal provided by the linear potentiometer 132 which is connected to the panel 116 through a connector 148 generally shown in FIG. 6 and more particularly shown in FIG. 9. The linear potentiometer 132 detects the position of the piston 56 in the pump 34 and generates a signal in correspondence with that position. That is, the linear potentiometer 132 converts the position into a corresponding electrical signal which is the "position" signal denoted in the drawings.

The circuits shown in FIGS. 7A–7B include means 150, responsive to the pump piston position signal, for providing a limit position signal in response to the signal from the linear potentiometer 132 corresponding to the piston 56 having moved to one of its limit positions, namely its lowest position for the illustrated embodiment. This limit position signal of the preferred embodiment is labeled "Y2" in FIG. 7B. The means 150 includes signal holding means 152 for providing the limit position signal Y2 as a constant electrical signal, namely a digital signal of a fixed binary value. The holding means 152 of the preferred embodiment includes an integrated circuit digital latch 154 which generates and holds the signal Y2 as a logic "1" in response to a setting signal from a comparing means for comparing the linear potentiometer position signal with a first preset electrical signal which represents the piston 56 being at one of its limit positions. The comparing means is implemented by the circuit 156 shown in FIG. 7A. The preset signal of the comparing means is set by the circuit 158. This preset signal in the preferred embodiment sets the threshold below which the "position" signal is detected as indicating that the piston 56 is at its lowest limit of movement within the pump 34.

Also shown in FIG. 7 is means 160, responsive to the pump piston position signal, for providing a limit position signal in response to the "position" signal corresponding to the piston 56 having moved to its other limit position, namely its uppermost position in the illustrated embodiment. The means 160 includes a signal holding means 162 which includes an integrated circuit digital latch 164. The latch 164 provides opposite logic level limit position signals Y1 (=logic 1) and Y1' (=logic 0) in response to the latch 164 being set by its corresponding setting means defined by comparing means for comparing the linear potentiometer position signal with a corresponding preset electrical signal representing the piston being at its other limit position. The comparing means includes the circuit 166, which includes the circuit 168 by which the preset signal is established to define the threshold above which the "position" signal is detected as indicating that the piston 56 is at its uppermost limit of movement within the pump 34.

The control circuits shown in FIGS. 7A-7B further include control means 170 (FIG. 7B) for controlling the various valve operating means which include the relays 146a-146h and the corresponding solenoid valves 68a-68h. The means 170 responds to the signals Y1, Y2 by producing a control signal T20. In response to either Y1=1 or Y2=1 in the preferred embodiment, T20 =0 which causes the relays 146a-146h to close their respective valves 38a-38h. That is, the control means 170 includes timing means for providing to the valve operating means a valve closing signal, T20=0, at a predetermined time after the latch 154 or the latch 164 provides its respective signal. The predetermined time includes the discharge time of a resistor capacitor network 171. The timing means also provides a valve opening signal, T20=1, at a predetermined time after the respective limit position signal Y1 or Y2 is removed. That is, when either the latch 154 or the latch 164 is set, the resulting Y2 or Y1 signal produces a T20 signal of suitable logic level through OR gate 172 to activate the relays 146a-146h so that the corresponding solenoid valves 68a-68h close the associated high pressure valves 38a-38h; and when the latches 154, 164 are reset (described hereinbelow), this removes the Y2 and Y1 signal (i.e., changes them to the opposite logic level) which causes the T20 logic level to switch after a predetermined time. The time is predetermined by a timing circuit 173 shown in FIG. 7, or more preferably by the alternative circuit 175 shown in FIG. 11, acting through the combinational logic of the OR gate 172.

Still referring to FIG. 7B a control means 174 responds to the Y2, Y1 signals for controlling the valve operating means which includes the relay 144 and the solenoid valve 66. These open and close the tank valve 30. The control means 174 includes timing means for providing a valve opening signal C4'=1 at a predetermined time (which includes the charging time of a resistor-capacitor network 177), which is after the predetermined time of the start of the valve closing signal T20=0, and also after the latch 154 or the latch 164 provides its respective output signal Y2=1 or Y1=1. This timing means also provides a valve o closing signal, C4'=0, at a predetermined time which commences before the predetermined start time for T20=1, but not necessarily after the respective output signal from the latch 154 or the latch 164 is removed (i.e., Y2=0 and Y1=0). That is, C4'=0 commences in the preferred embodiment after a timing circuit 178 times out after being activated by Y1=1 or Y2=1. The C4' signal is provided in response to the combinational logic of an OR gate 176, to one input of which the timing circuit 178 is connected.

The latches 154, 164 are reset (Y2=0, Y1=0) by means 180 which is responsive to the "position" signal from the linear potentiometer 132 corresponding to the piston 56 having moved away from either of its limit positions. The means 180 includes comparing means for comparing the "position" signal with a preset electrical signal representing the piston 56 being at a predetermined position between the two limit positions. This is implemented by a circuit 182, and the preset electrical signal is set by a circuit 184 shown in FIG. 7A. The set point of the illustrated circuit 184 represents the piston 56 being at substantially the midpoint of its stroke between its two end limit positions. The output of the comparing means is connected to the clear, or reset, inputs of the latches 154, 164 as shown in FIG. 7. Resetting of the latches 154, 160 switches the logic levels of the control signals Y1, Y1', Y2 from their set logic levels (Y1=1, Y1'=0, Y2=1) to their reset logic levels (Y1=0, Y1'=1, Y2=0).

The latches 154, 164 can be disabled by means of the T15 signal provided by the local/remote switch 12. The T15 signal is connected to the NAND logic gates 186, 188 shown in FIG. 7A. When the switch 12 is in the "remote" position, T15=0 so that the latches 154, 164, and thus the control circuitry shown in FIGS. 7A-7B, are disabled.

The circuits shown in FIGS. 7A-7B provide means not only for opening and closing the valves 30, 38a-38h, but also means for operating the valves 90, 100 to automatically move the piston 56 away from either of its limit positions when it has been detected that the piston 56 has reached a limit position. That is, the signals Y1, Y1', Y2 are applied to the combinational logic circuits shown in FIG. 8 connected to the relays 134, 136, 138, 140, 142. It is to be noted that these combinational logic circuits also provide means for connecting the relays 134–142 to the connector 135 terminals (FIG. 9) through which the D1-D5 data signals can be received from the external controller 4 so that the position of the piston 56 can also be controlled by the external controller 4. The T1-T4 signals shown in FIG. 8 are not implemented in the illustrated embodiment, but they can be if desired. The T5 signal is implemented, and is provided by the pump retract switch 20.

Other combinational logic circuits shown in FIG. 8 include a NAND gate 190 which combines the T6 signal from the tank valve switch 18, the D6 data line from the respective connector 135 terminal, and the C4' control signal from the control circuits 174 shown in FIG. 7B.

The remaining combinational logic circuits shown in FIG. 8 are for the individual channels 36a–36h, each of which circuits includes a respective NAND gate 192 for logically combining the signal from the respective switch 16, the respective data line from the connector 135 terminal, and the T20 signal from the control circuit 170 shown in FIG. 7.

The aforementioned data lines are provided through buffers 194, 196 shown in FIG. 9. The inputs of the buffers are connected to the ribbon cable 126 at the connector 135. The buffers 194, 196 are enabled/disabled by means of the combinational logic circuit 200 whose inputs are the T15 (switch 12), T16 (switch 14), and T20 (control circuit 170) signals.

Associated with data lines D1, D3 of the preferred embodiment are switches 202 which are manually set to permit pump control pressure to be set either manually through the regulator 88 or electronically through the electronic air regulator 6 which can be connected to the air supply inlet 72 and channeled through the valve 86 (FIG. 5B). If the electronic air regulator 6 is used, it is controlled by an analog voltage provided at the output of a digital-to-analog converter (DAC) 204 shown in FIG. 10. The inputs of the DAC 204 are provided by counters 206a, 206b, 206c which are driven in response to a signal from a clock 208 in FIG. 10 and the "up" and "down" signals from FIG. 9 as coupled through the combinational logic circuit 210. A reset circuit 212 is also provided in the electronic air regulator control circuit shown in FIG. 10. The analog voltage provided at the output of the DAC 204 is provided through a connector 214.

Also shown in FIG. 9 is a connector 216 for making the indicated power connections.

OPERATION

When the local/remote switch 12 is in the "local" position, the circuits shown in FIGS. 7A-7B are active so that the piston 56 is automatically moved away from either of its limits of movement within the pump 34 to maintain pressure in one or more of the selected channels 36. This automatic control provided wholly within the housing 2 is deactivated by the T15 signal acting through the NAND gates 186, 188 shown in FIG. 7A when the switch 12 is in the "remote" position.

When the computer/manual switch 14 is in the "computer" position, the valve 84 shown in FIG. 5 is controlled to pass air from the valve 86 to the valve 90. When the switch 14 is in the "manual" position, valve 84 communicates the air flow from the regulator 88 to the valve 90. Also when the switch 14 is in the "manual" position, the signal T16 from the switch 14 disables D1 from affecting operation of the valve 86 through the combinational logic circuit 114 shown in FIG. 8.

When the local/remote switch 12 is in the "local" position and the computer/manual switch 14 is in the "manual" position, the buffers 194, 196 shown in FIG. 9 are disabled; otherwise, these buffers are enabled to allow communication and control from the external controller 4 via the data lines D1–D14, except when the buffer 196 is disabled by T20=0, which is generated to close the valves 38a–38h upon the piston 56 reaching either of its extreme positions regardless of the settings of the T7–T14 or D7–D14 signals.

Because operation in the "remote" position setting of the switch 12 calls for external control which is not within the scope of the present invention as claimed herein, only operation in the local/manual mode and the local/computer mode will be described.

When the switch 12 is in the "local" position and the switch 14 is in the "manual" position, the buffers 194, 196 are disabled as just described so that control is entirely through the components of the front panel 8. Assuming that autoclaves, for example, to be pressurized have been connected to respective ones of the channels 36a–36h, and further assuming that a municipal water supply, for example, and pressurized air supply, for example, have been connected to the pressurizing fluid inlet coupling 44 and control fluid inlet coupling 72, respectively, the tank valve 30 is opened using the switch 18 and the respective valves 38a–38g to which autoclaves have been connected are opened using the switches 16a–16h. Water, or other pressurizing fluid, flows in through the open tank valve 30 until the system is adequately filled. The tank valve 30 and the opened valves 38a–38h are then closed by their respective front panel switches, and the pressure is brought up to the desired point by manipulating the control knob 28 of the air regulator 88. This pressure is displayed at least by the pressure gauge 22. This adjusts the air pressure applied to the piston 56 to thereby move the piston 56 to decrease or increase the effective volume of the pressurizing circuit to obtain the desired pressure. Once this pressure is attained, the channels which are to be brought up to this pressure are opened by actuating the respective switches 16a–16h. It is contemplated that this mode of operation is most suited for controlling only one channel and connected device or several channels and connected devices which are to be maintained together at the same pressure; however, different pressures can be created in the pressurizing system and communicated to individual or groups of channels to bring connected devices up to selected pressures by sequentially manually operating the controls on the front panel 8. This type of manual multiplexing renders the automatic pressure control aspect of the circuitry shown in FIGS. 7 and 8 ineffective with respect to those channels which are not continuously in communication with the pressurizing circuit.

For that channel, or that group of channels simultaneously communicating with the fluid circuit pressurized by the pump 34, automatic pressure control is maintained by the electrical circuits shown in FIGS. 7 and 8 and the pump control fluid circuit shown in FIG. 5B. To pressurize a device connected to a channel 36, the respective valve 38 is opened by proper actuation of the respective switch 16 as just described. The switch 16 is left in the valve open position. Because of this, in the specific application of an autoclave being connected to the respective channel, a pressure change may occur in the system through expansion of the thickening/hardening cement sample in the autoclave, or, more generally through leakage in the system, for example. Any of these changes within the system can cause the piston 56 to move to either its lower limit position or its upper limit position ("lower" and "upper" for the orientation shown in FIG.2). When either of these extremes is reached, the respective comparing means 156, 166 will detect this and set the respective latch 154, 164. For the latch which is set, the respective limit position signal Y1 or Y2 will switch to the high logic level and be communicated through a logic NOR gate 218 shown in FIG. 7B to the opposite logic level. The signal from the NOR gate 218 operates the control circuits 170, 174 to first switch the logic level of the T20 signal to the logic level by which each of the relays 146a–146h is controlled to operate the respective solenoid valve 68a–68h to close its respective valve 38a–38h, and then to switch the C4' signal to have a logic level which operates the relay 144 to control the solenoid valve 66 to open the tank valve 30. This isolates each of the channels 36 from the main pressurizing circuit and opens that circuit to the water source or drain through the tank valve 30.

After the channel valves 38a–38h have been closed and the tank valve 30 has been opened, the piston 56 will be automatically moved back to its center point (or other location predetermined by the setting of the circuit 184 in FIG. 7A) by operation of the valves 90, 100 controlled by the Y1, Y1' and Y2 signals applied to the combinational logic circuits operating the relays 138, 142 (relays 136, 140 not used in the preferred embodiment) as shown in FIG. 8. It is to be recalled that the valve 86 operated by the relay 134, is not used in the local/manual mode and that the valve 84 is communicating the manually controlled air regulator 88 pressure to the valve 90.

When the piston 56 has been centered, this is detected by the resetting circuit 180. Once the set latch has been reset by the circuit 180, the change in the logic level of the reset Y1, Y2 signal switches the output of the gate 218. This starts the timing circuit 173 (FIG. 7B) or 175 (FIG. 11) to delay switching the T20 signal so that the valves 38 remain closed for the duration of the timing signal. This allows the system pressure to stabilize after the prior closure of the tank valve 30, which occurs when the timing circuit 178 times out after having been initiated by the setting of the Y1 or Y2 signal upon the piston 56 reaching one of its extremes.

The foregoing automatic control also occurs in the local/computer mode. When the switch 14 is in the "computer" position, however, the circuitry shown in FIG. 8 is also responsive to the D1–14 signals received through the enabled buffers 194, 196 shown in FIG. 9. Furthermore, the air regulation must be by an external device because the valve 86 is now active and connected to the valve 84, which has been switched by the front panel switch 14 being moved to the "computer" position. Such an external air regulation device can be controlled by the circuitry shown in FIG. 10 as described hereinabove. As previously mentioned, the D7–D14 signals are disabled by the T20 signal when pressure is to be automatically corrected if the piston 56 moves to one of its extremes.

It is in the local/computer mode that the multiplexing feature of the present invention is more efficiently implemented. In this mode, the externally connected controller 4, such as a microcomputer, controls the system pressure, selects the channels to be pressurized, reads the position of the piston 56, and monitors the individual channel pressures via the pressure transducers 42a–42h. To achieve the multiplexing control, the external controller 4 compares each channel pressure with a prescribed set point entered into the controller for that channel. If the actual channel pressure is different from the prescribed set point: the pump 34 is actuated, via the pump control fluid circuit in FIG. 5B and its electrical control circuits in FIG. 8 as operated by the controller 4, to place the system pressure at the particular channel's current pressure; the respective valve 38a–38h for the selected autoclave is opened; the pump 34 is further controlled to adjust the pressure to the desired level; and then the channel valve is closed. This control is effected by means of the external controller 4 transmitting the suitable combination of data signals D1–D14 through the input buffers 194, 196 to the circuits shown in FIG. 8. This sequence is repeated for each channel as needed.

The present invention allows a small single-stroke intensifier pump to be used to automatically maintain pressures in autoclaves connected to the pump despite pressure changes which are due to, for example, expansions and loss of fluid through leaks. The present invention also permits multiplexing a number of autoclaves for pressurization by a single pressurizing pump. This reduces relative space requirements and costs. Although the present invention permits manual multiplexing and provides automatic control within itself, it is also adapted to receive computer or other external control which permits more efficient multiplexing and which permits a number of channels to be controlled to different pressure schedules if desired. Because pump piston position and pressure changes are detectable by an external controller, the compressability of the samples contained within the connected pressurized devices can be computed.

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

What is claimed is:

1. An automatic pressure control apparatus, comprising:
   a pump including a chamber defined therein and further including a piston disposed in said chamber so that said piston is movable between a first limit position and a second limit position;
   a first valve;
   first valve operating means, connected to said first valve, for opening and closing said first valve;
   a second valve;
   second valve operating means, connected to said second valve, for opening and closing said second valve;
   fluid conducting means for connecting said chamber of said pump and said first and second valves;
   detector means, connected to said pump, for generating a signal in correspondence with the position of said piston within said pump;
   means, connected to said detector means, for providing a first limit position signal in response to said signal of said detector means corresponding to said piston having moved to said first limit position;
   means, connected to said detector means, for providing a second limit position signal in response to said signal of said detector means corresponding to said piston having moved to said second limit position;
   first control means, connected to said means for providing a first limit position signal and to said means for providing a second limit position signal, for controlling said first valve operating means to close said first valve in response to either said first limit position signal or said second limit position signal;

second control means, connected to said means for providing a first limit position signal and to said means for providing a second limit position signal, for controlling said second valve operating means to open said second valve in response to either said first limit position signal or said second limit position signal;

means, connected to said means for providing a first limit position signal and to said means for providing a second limit position signal, for moving said piston away from said first or second limit position in response to the respective one of said first or second limit position signal; and means, connected to said detector means, for operating said second control means and said first control means to control said second valve operating means and said first valve operating means, respectively, to close said second valve and to open said first valve, respectively, in response to said signal of said detector means corresponding to said piston having moved away from said first and second limit positions.

2. An apparatus as defined in claim 1, wherein:

said means for providing a first limit position signal includes first signal holding means, connected to said first and second control means and to said means for moving said piston away, for providing said first limit position signal as a constant electrical signal;

said means for providing a second limit position signal includes second signal holding means, connected to said first and second control means and to said means for moving said piston away, for providing said second limit position signal as a constant electrical signal;

said means for operating said second control means and said first control means includes means, connected to said first and second signal holding means, for causing said first and second signal holding means to remove said constant electrical signals thereof in response to said signal of said detector means corresponding to said piston having moved away from said first or second limit position;

said first control means includes first timing means, connected to said first signal holding means and said second signal holding means, for providing to said first valve operating means: a first valve closing signal at a predetermined time after said first signal holding means or said second signal holding means provides its respective said constant electrical signal; and a first valve opening signal at a predetermined time after the respective said constant electrical signal is removed; and said second control means includes second timing means, connected to said first signal holding means and said second signal holding means, for providing to said second valve operating means: a second valve opening signal at a predetermined time, which is after said predetermined time for said first valve closing signal, after said first signal holding means or said second signal holding means provides its respective said constant electrical signal; and a second valve closing signal at a predetermined time, which is before said predetermined time for said first valve opening signal, after the respective said constant electrical signal is removed.

3. An apparatus as defined in claim 1, wherein:

said means for providing a first limit position signal includes a first digital latch and means for setting said first digital latch in response to said signal of said detector means corresponding to said piston having moved to said first limit position;

said means for providing a second limit position signal includes a second digital latch and means for setting said second digital latch in response to said signal of said detector means corresponding to said piston having moved to said second limit position;

said means for operating said second control means and said first control means includes means for resetting said first and second digital latches in response to said signal of said detector means corresponding to said piston having moved away from said first and second limit position;

said first control means includes first timing means, connected to said first and second digital latches, for enabling said first valve operating means to close said first valve after said first or second digital latch is set and for enabling said first valve operating means to open said first valve after said first and second digital latches are reset; and said second control means includes second timing means, connected to said first and second digital latches, for enabling said second valve operating means to open said second valve after said first valve is closed and for enabling said second valve operating means to close said second valve after said first and second digital latches are reset but before said first valve opens.

4. An apparatus as defined in claim 1, wherein:

said first valve includes high pressure valve means for connecting said fluid conducting means to an autoclave; and said second valve includes high pressure valve means for connecting said fluid conducting means to a fluid source.

5. An apparatus as defined in claim 1, wherein said means for moving said piston away from said first or second limit position includes:

valve means for selectably communicating a pump driving fluid to said pump to move said piston therein;

actuating means for actuating said valve means;

means for connecting said actuating means to said means for providing a first limit position signal and to said means for providing a second limit position signal so that said actuating means responds to said first and second limit position signals; and means for connecting said actuating means to a computer so that said actuating means is responsive to computer control.

6. An apparatus as defined in claim 1, wherein:

said means for providing a first limit position signal includes:

a first comparator circuit having an input connected to said detector means; and a first latch connected to said first comparator circuit;

said means for providing a second limit position signal includes:

a second comparator circuit having an input connected to said detector means; and a second latch connected to said second comparator circuit;

said first control means includes a first timing circuit connected to said first and second latches;

said second control means includes a second timing circuit connected to said first and second latches;

said first valve operating means includes a first solenoid valve connected to said first valve and said first timing circuit; and said second valve operating means includes a second solenoid valve connected to said second valve and said second timing circuit.

7. An apparatus for controlling an autoclave valve, a tank valve and a piston of a pump within a fluid circuit for pressurizing an autoclave, said apparatus comprising:

means for converting the position of the piston into a corresponding electrical signal;

first comparing means for comparing the corresponding electrical signal with a first preset electrical signal representing the piston being at a first position;

second comparing means for comparing the corresponding electrical signal with a second preset electrical signal representing the piston being at a second position;

third comparing means for comparing the corresponding electrical signal with a third preset electrical signal representing the piston being at a predetermined position between the first and second positions;

a first latch connected to said first and third comparing means so that said first latch is set when the comparison of the corresponding electrical signal and the first preset electrical signal by said first comparing means indicates the piston is at the first position and so that said first latch is reset when the comparison of the corresponding electrical signal and the third preset electrical signal by said third comparing means indicates the piston is at the predetermined position between the first and second positions;

a second latch connected to said second and third comparing means so that said second latch is set when the comparison of the corresponding electrical signal and the second preset electrical signal by said second comparison means indicates the piston is at the second position and so that said second latch is reset when the comparison of the corresponding electrical signal and the third preset electrical signal by said third comparing means indicates the piston is at the predetermined position between the first and second positions;

first timing means, connected to said first and second latches, for providing a first timing signal for closing and opening the autoclave valve in response to the setting and resetting of said first and second latches; and second timing means, connected to said first and second latches, for providing a second timing signal for opening and closing the tank valve in response to the setting and resetting of said first and second latches.

8. An apparatus as defined in claim 7, further comprising means, connected to said first and second latches, for moving the piston in response to the setting and resetting of said first and second latches.

9. A method of controlling pressure in an autoclave, comprising:

a) connecting an autoclave to a first valve of a fluid circuit, which fluid circuit further includes a second valve through which a fluid source communicates with the fluid circuit and which fluid circuit also includes a piston movable between first and second positions within the fluid circuit;

b) pressurizing the fluid circuit and the autoclave to a selected pressure with fluid from the fluid source, including controlling the first valve, the second valve and the piston so that when the selected pressure is obtained, the first valve is open, the second valve is closed and the piston is not at either the first position or the second position; and c) automatically detecting, through an electrical circuit responsive to the position of the piston, if the piston moves to either the first position or the second position and thereupon automatically through the electrical circuit sequentially closing the first valve, opening the second valve, moving the piston to a predetermined position between the first and second positions, closing the second valve, and opening the first valve.

10. A method as defined in claim 9, wherein step c) includes: converting the position of the piston into a corresponding electrical signal;

comparing the corresponding electrical signal with a first preset electrical signal representing the piston being at the first position;

comparing the corresponding electrical signal with a second preset electrical signal representing the piston being at the second position;

comparing the corresponding electrical signal with a third preset electrical signal representing the piston being at the predetermined position between the first and second positions;

setting a first latch when the comparison of the corresponding electrical signal and the first preset electrical signal indicates the piston is at the first position;

setting a second latch when the comparison of the corresponding electrical signal and the second preset electrical signal indicates the piston is at the second position;

resetting the first and second latches when the comparison of the corresponding electrical signal and the third preset electrical signal indicates the piston is at the predetermined position between the first and second positions;

closing the first valve and opening the second valve in response to setting the first latch or the second latch ;

closing the second valve and opening the first valve in response to resetting the first and second latches; and moving the piston in response to setting and resetting the first and second latches.

11. A pressure control apparatus for a plurality of autoclaves, comprising:

a pump;

a plurality of valves, each of said valves dedicated for connecting to a respective autoclave;

fluid conducting means for connecting said pump and said valves;

pressure control means, connected to said pump, for controlling said pump to provide a selected pressure within said fluid conducting means; and valve control means, connected to said valves, for selectably controlling said valves so that a selected valve can be opened to communicate a selected pressure provided in said fluid conducting means to an autoclave connected to the selected valve.

12. An apparatus as defined in claim 11, wherein said valve control means includes:
 a plurality of manual switches;
 a plurality of terminals for receiving data signals from a computer; and
 a plurality of valve actuating means, each said valve actuating means connected to a respective one of said switches and to a respective one of said terminals for operating a respective one of said valves in response either to operation of the respective one of said switches or to a computer data signal communicated through the respective one of said terminals.

13. An apparatus as defined in claim 11, wherein said pressure control means includes:
 pump control valve means for communicating a pump driving fluid pressure to said pump;
 means, connected to said pump control valve means, for manually selecting a first pump driving fluid pressure;
 means, connected to said pump control valve means, for communicating, in response to control from a computer, a second pump driving fluid pressure to said pump control valve means; and
 switch means, connected to said pump control valve means, for selecting which of said first pump driving fluid pressure and said second pump driving fluid pressure is passed by said pump control valve means.

14. An apparatus as defined in claim 13, wherein said means for communicating a second pump driving fluid pressure includes:
 an inlet valve including an output connected to said pump control valve means and further including input means for receiving the second pump driving fluid pressure from an electronic air regulator;
 means for operating said inlet valve in response to control from the computer; and
 means for controlling the electronic air regulator in response to control from the computer.

15. An apparatus as defined in claim 11, wherein: said pump includes a piston;
 said apparatus further comprises:
 main flow valve means, connected to said fluid conducting means, for communicating a pressurizing fluid source with said fluid conducting means;
 main flow valve operating means for opening and closing said main flow valve means;
 detector means, responsive to the position of said piston, for generating a signal in correspondence with the position of said piston;
 means, responsive to said signal of said detector means, for providing a second limit position signal in response to said signal of said detector means corresponding to said piston having moved to said first limit position; means, responsive to said signal of said detector means, for providing a second limit position signal in response to said signal of said detector means corresponding to said piston having moved to said second limit position;
 first control means, responsive to said first and second limit position signals, for controlling said valve control means to close said plurality of valves in response to either said first limit position signal or said second limit position signal; and
 second control means, responsive to said first and second limit position signals, for controlling said main flow valve operating means to open said main flow valve means in response to either said first limit position signal or said second limit position signal.

16. An apparatus as defined in claim 15, wherein said pressure control means includes:
 means for selectably communicating a pump driving fluid to said pump to move said piston therein;
 actuating means for actuating said means for selectably communicating;
 means for connecting said actuating means to said means for providing a first limit position signal and to said means for providing a second limit position signal so that said actuating means responds to said first and second limit position signals; and
 means for connecting said actuating means to a computer so that said actuating means is responsive to computer control.

17. An apparatus as defined in claim 11, wherein: said pump includes a piston; and
 said apparatus further comprises:
 main flow valve means, connected to said fluid conducting means, for communicating a pressurizing fluid source with said fluid conducting means;
 means for converting the position of the piston into a corresponding electrical signal;
 first comparing means for comparing the corresponding electrical signal with a first preset electrical signal representing the piston being at a first position;
 second comparing means for comparing the corresponding electrical signal with a second preset electrical signal representing the piston being at a second position;
 third comparing means for comparing the corresponding electrical signal with a third preset electrical signal representing the piston being at a predetermined position between the first and second positions;
 a first latch connected to said first and third comparing means so that said first latch is set when the comparison of the corresponding electrical signal and the first preset electrical signal by said first comparing means indicates the piston is at the first position and so that said first latch is reset when the comparison of the corresponding electrical signal and the third preset electrical signal by said third comparing means indicates the piston is at the predetermined position between the first and second positions;
 a second latch connected to said second and third comparing means so that said second latch is set when the comparison of the corresponding electrical signal and the second preset electrical signal by said second comparison means indicates the piston is at the second position and so that said second latch is reset when the comparison of the corresponding electrical signal and the third preset electrical signal by said third comparing means indicates the piston is at the predetermined position between the first and second positions;

first timing means, connected to said first and second latches, for providing a first timing signal for closing and re-opening open ones of said plurality of valves in response to the setting and resetting of said first and second latches; and second timing means, connected to said first and second latches, for providing a second timing signal for opening and closing said main flow valve means in response to the setting and resetting of said first and second latches.

18. A method of controlling pressure in a plurality of autoclaves, each autoclave connected to a respective one of a plurality of valves of a fluid circuit, which fluid circuit further includes a pump connected to said valves, said method comprising:

a) operating the pump to pressurize the fluid circuit to a selected pressure;

b) opening and closing at least one valve to communicate the selected pressure to the autoclave connected thereto; and c) repeating steps a) and b) until selected autoclaves are pressurized to respective selected pressures in response to operation of the pump.

19. A method as defined in claim 18, further comprising:

d) monitoring the pressure in each pressurized autoclave; and e) repeating steps a) and b) in response to step d) to maintain the respective selected pressures in the respective pressurized autoclaves.

* * * * *